(12) United States Patent
Benner et al.

(10) Patent No.: US 10,829,812 B1
(45) Date of Patent: *Nov. 10, 2020

(54) AMPLIFICATION OF OLIGONUCLEOTIDES CONTAINING NON-STANDARD NUCLEOTIDES

(71) Applicants: Steven A Benner, Gainesville, FL (US); Roberto Laos, Gainesville, FL (US); Nicole A Leal, Gainesville, FL (US); Zunyi Yang, Gainesville, FL (US); Myong Jung Kim, Gainesville, FL (US)

(72) Inventors: Steven A Benner, Gainesville, FL (US); Roberto Laos, Gainesville, FL (US); Nicole A Leal, Gainesville, FL (US); Zunyi Yang, Gainesville, FL (US); Myong Jung Kim, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/216,266

(22) Filed: Dec. 11, 2018

Related U.S. Application Data

(63) Continuation-in-part of application No. 15/584,728, filed on May 2, 2017, now abandoned, which is a continuation-in-part of application No. 14/746,243, filed on Jun. 22, 2015, now Pat. No. 9,637,783.

(51) Int. Cl.
*C12Q 1/686* (2018.01)
*C12Q 1/6853* (2018.01)
*C12Q 1/6806* (2018.01)

(52) U.S. Cl.
CPC .......... *C12Q 1/686* (2013.01); *C12Q 1/6806* (2013.01); *C12Q 1/6853* (2013.01); *C12Q 2525/117* (2013.01)

(58) Field of Classification Search
None
See application file for complete search history.

(56) References Cited

U.S. PATENT DOCUMENTS 9,637,783 B1 * 5/2017 Benner .................. C12P 19/34

OTHER PUBLICATIONS

Sismour et al (Nucleic Acids Research, 32(2): 728-735, 2004) (Year: 2004).*

* cited by examiner

*Primary Examiner* — Richard A Schnizer

(57) ABSTRACT

This invention relates to processes that amplify oligonucleotide analogs that incorporate non-standard nucleobase analogs from an artificially expanded genetic information system. These pair in DNA duplexes via patterns of hydrogen bonds that differ from patterns that join the thymine-adenine and guanine-cytosine nucleobase pairs.

3 Claims, 8 Drawing Sheets pyADD
Acceptor
Donor
Donor puDAA
Donor
Acceptor
Acceptor

V    J pyADA
Acceptor
Donor
Acceptor puDAD
Donor
Acceptor
Donor

T    A pyDAD
Donor
Acceptor
Donor puADA
Acceptor
Donor
Acceptor

K    X pyDDA
Donor
Donor
Acceptor puAAD
Acceptor
Acceptor
Donor

Z    P

AMPLIFICATION OF OLIGONUCLEOTIDES CONTAINING NON-STANDARD NUCLEOTIDES

CROSS REFERENCE TO RELATED APPLICATIONS

This application is a continuation-in-part, and claims the benefit, of U.S. patent application Ser. No. 15/584,728 (currently pending, filed 2 May, 2017), for "Amplification of oligonucleotides containing non-standard nucleotides". U.S. patent application Ser. No. 15/584,728 is itself a continuation-in-part of Ser. No. 14/746,243 (filed 22 Jun. 2015), now issued as U.S. Pat. No. 9,637,783.

STATEMENT OF RIGHTS TO INVENTIONS MADE UNDER FEDERALLY-SPONSORED RESEARCH

This invention was made with government support under grants from the National Science Foundation (MCB-1412869 and CHE 1507816). The government has certain rights in the invention.

THE NAMES OF PARTIES TO A JOINT RESEARCH AGREEMENT

Not applicable

INCORPORATION BY REFERENCE OF MATERIAL SUBMITTED ON A COMPACT DISK

None

BACKGROUND OF THE INVENTION

1. Field of the Invention

This invention relates to nucleotide analogs and their derivatives (termed non-standard nucleotides) that, when incorporated into DNA and RNA, expand the number of replicatable nucleotides beyond the four found in standard DNA and RNA. The invention further relates to processes that incorporate those non-standard nucleotide analogs into oligonucleotide products using the corresponding triphosphate derivatives, and more specifically, polymerases and non-standard nucleoside triphosphates that support the polymerase chain reaction (PCR) with these, including PCR where the products contain more than one non-standard nucleotide. This application is a continuation-in-part of U.S. patent application Ser. No. 14/746,243, whose disclosure is incorporated in its entirety by reference.

2. Description of the Related Art

Natural oligonucleotides bind to complementary oligonucleotides according to the well-known rules of nucleobase pairing first elaborated by Watson and Crick in 1953, where adenine (A) pairs with thymine (T) (or uracil, U, in RNA), and guanine (G) pairs with cytosine (C), with the complementary strands anti-parallel to each other. These rules arise from two principles of complementarity, size-complementarity (large purines pair with small pyrimidines) and hydrogen bonding complementarity (hydrogen bond donors pair with hydrogen bond acceptors).

It is now well established in the art that the number of independently replicable nucleotides in DNA can be increased, where the size- and hydrogen binding complementarities are retained, but where different heterocycles (nucleobase analogs) attached to the sugar-phosphate backbone implement different hydrogen bonding patterns. As many as eight different nucleobase analogs forming four additional nucleobase pairs are conceivable (see, for example, [Benner, S. A. (1995) Non-standard Base Pairs with Novel Hydrogen Bonding Patterns. U.S. Pat. No. 5,432,272 (Jul. 11, 1995)]). This has led to an "artificially expanded genetic information system" (AEGIS). The ability of pairing between the additional nucleobase pairs to support DNA duplex stability has had substantial use in diagnostics. In this disclosure, DNA includes oligonucleotides containing AEGIS nucleic acids and their analogs in linear and non-linear topologies, including as dendrimers, comb-structures, and nanostructures, and these oligonucleotides and their analogs carrying tags (e.g., fluorescent, functionalized, or binding) to the ends, sugars, or nucleobases.

It would be useful to amplify oligonucleotides containing AEGIS components in processes analogous to the well-known polymerase chain reaction (PCR), here defined as a process involving thermal cycling, where the heat step denatures a duplex formed at each cycle to allow a new set of primers to bind. If PCR could be implemented with expanded DNA AEGIS alphabets, it would have many uses, including (without limitation) DNA and RNA-targeted diagnostics, and in vitro selection and evolution to create catalysts, ligands, and receptors.

Various items in the art describe efforts to use the U.S. Pat. No. 5,432,272 nucleobases with polymerases to support PCR. However, these generally failed to sustain PCR over more than five heat-cool cycles, since polymerases that incorporate non-standard base pairs into duplexes with sufficient efficiency and fidelity to support PCR were not described. This failure is illustrated by Johnson et al. [Johnson, S. C., Sherrill, C. B., Marshall, D. J., Moser, M. J., Prudent, J. R. (2004) A third base pair for the polymerase chain reaction: inserting isoC and isoG. $Nucl.\ Acids\ Res.$ 32, 1937-1941], who attempted to incorporate the isocytosine and isoguanine disclosed in U.S. Pat. No. 5,432,272 into PCR. As their publication shows, the non-standard component is not retained in the product, to an extent greater than 90% over 5 cycles. Indeed, their FIG. 2 showed that only ~90% of the isoC:isoG pair remained after just one cycle, and only ~80% was retained after seven cycles. This can be used as a metric for the utility of a PCR process that incorporates a non-standard nucleobase pair. In this case, the loss was attributed to the ability of a minor tautomeric form of isoguanosine to pair with thymidine, as well as contacts that thermostable polymerases (the kind that are needed for useful PCR, as they survive heating to at least 80° C. for the purpose of separating strands) make to unshared electrons in the minor groove, which are delivered by DNA from the exocyclic C=O groups of C and T, and N3 of A and G.

Many enzymes work well with AEGIS components, including kinases, ligases, and even ribosomes [Bain, J. D., Chamberlin, A. R., Switzer, C. Y., Benner, S. A. (1992) Ribosome-mediated incorporation of non-standard amino acids into a peptide through expansion of the genetic code. $Nature$ 356, 537-539]. Polymerases, in contrast, accept many non-standard components of DNA only inefficiently, judging by rate, processivity, fidelity, or some combination of these [Horlacher, J., Hottiger, M., Podust, V. N., Hübscher, U. and Benner, S. A. (1995) Expanding the genetic alphabet: Recognition by viral and cellular DNA polymerases of nucleosides bearing bases with non-standard hydrogen bonding patterns. *Proc. Natl. Acad. Sci.* 92, 6329-6333]. These inefficiencies need not prevent the utility of polymerase-based incorporation of AEGIS components in single pass experiments, and may not be apparent with standing start experiments, where the non-standard triphosphate is the first nucleotide to be added to a primer, or a running start experiment, where the polymerase adds standard nucleotides before it is challenged to incorporate a non-standard nucleotide. However, they defeat sustained amplification by PCR where over 90% of the nucleobase is retained after the first theoretical cycle, here defined as "useful PCR".

Thus, U.S. Pat. No. 5,432,272 nor the prior art do not enable useful PCR of DNA containing non-standard nucleotides (AEGIS components). While it is recognized by those of ordinary skill in the art, and taught here, that PCR processes invariably introduce some mutations, and that some daughter oligonucleotides will not have the exact identical sequence as the original oligonucleotide (and indeed, sequence evolution due to this infidelity is useful for doing in vitro evolution, see U.S. Pat. No. 8,586,303), PCR amplification of these oligonucleotides would be most useful if the level of mutation is lower rather than higher, preferably less than a 5% loss of the non-standard nucleobase per cycle, and more preferably less than a 2% loss of the non-standard nucleobase per cycle, and in any case retaining 90% of the AEGIS component after the first cycle.

U.S. Pat. No. 8,354,225 (Ser. No. 11/371497) attempted to achieve a less ambitious process, here with an extra nucleotide pair formed between diaminopyrimidine and either xanthosine or 5-aza-7-deazaxanthosine, one that did not involve thermocycling. This was shown to be possible with a mutant form of the reverse transcriptase from HIV. Unfortunately, reverse transcriptases are not thermally stable upon heating to 80° C. (or, in most cases, even above 50° C.), and therefore cannot support PCR. Indeed, U.S. Pat. No. 8,354,225 required an addition of more reverse transcriptase after each heat step. Further, the other pyrimidine nucleoside analogs that U.S. Pat. No. 8,354,225 disclosed had nucleobases based on a pyrazine ring system, now known to epimerize rapidly. Finally, the structure disclosed by U.S. Pat. No. 8,354,225 to implement the purine analog with a hydrogen bond donor-donor-acceptor pattern is now known to be nonfunctional, and the pyrimidine analog shown to implement the hydrogen bond donor-donor-acceptor pattern lacks a methyl group and is now known to be unstable with respect to depyrimidinylation. FIG. 1 summarizes these deficiencies.

For these reasons, despite the widespread recognition of the value of PCR using non-standard nucleobases, if it could be achieved, many in the art considered this goal unachievable.

BRIEF SUMMARY OF THE INVENTION

This invention covers processes for the amplification of oligonucleotides that incorporate designated components of an artificially expanded genetic information system (FIGS. 2 and 3), as well as the compositions of matter that those amplifications produce, as well as polymerases that accept them.

DESCRIPTION OF THE INVENTION

Figure 1:
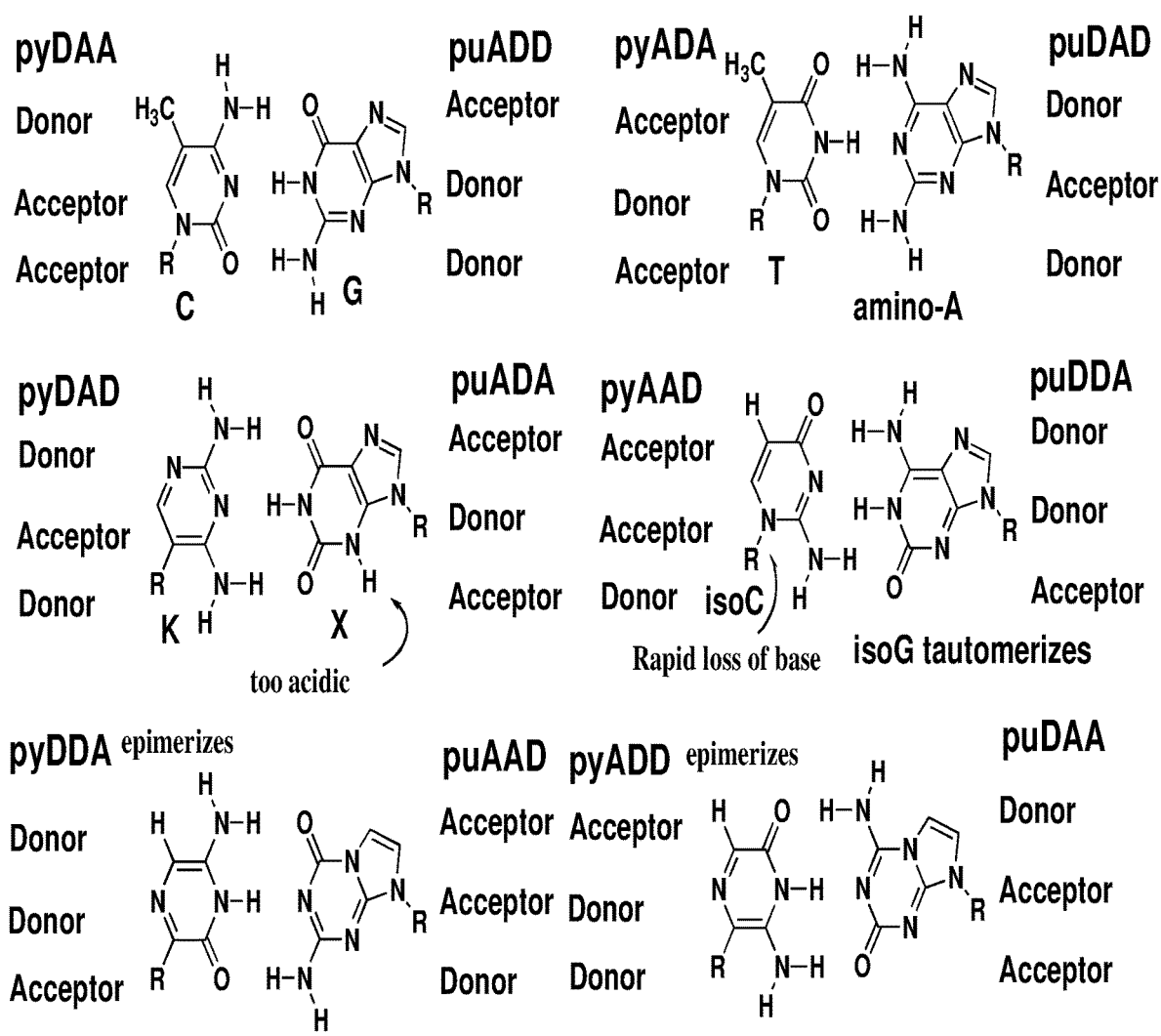
FIG. 1. Implementations of AEGIS nucleobases disclosed by U.S. Pat. No. 8,354,225. The nucleobase implementing the puDDA pattern suffers from large tautomeric ambiguity. The implementations on pyrazine rings suffer from facile epimerization. The implementation on a simple pyridine is too basic and prone to oxidation.
Figure 2:
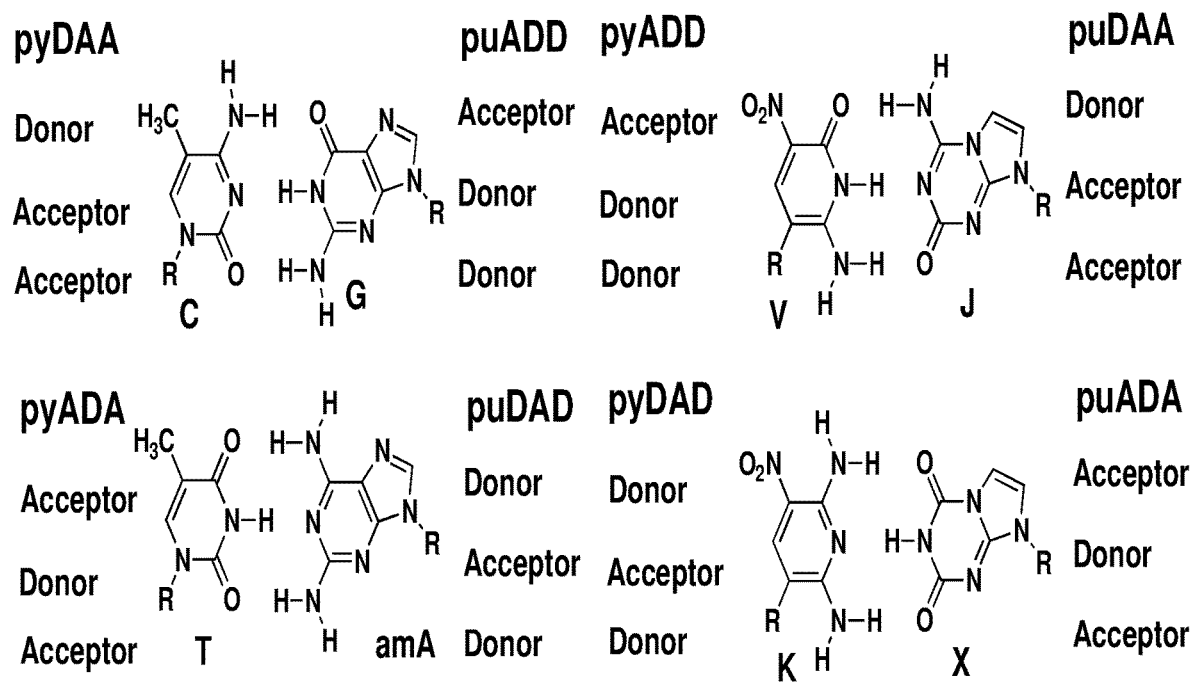
FIG. 2. The presently preferred embodiments of some of the non-standard AEGIS nucleobases and their pairs. These have a Watson-Crick geometry, with large purines or purine analogs (indicated by "pu") pairing with small pyrimidines or pyrimidine analogs (indicated by "py") joined by hydrogen bonds. The hydrogen-bonding acceptor (A) and donor (D) groups are listed from the major to the minor groove as indicated. Electron density presented to the minor groove is shown by the shaded lobes. Note that some non-standard pyrimidines do not present this density.
Figure 3:
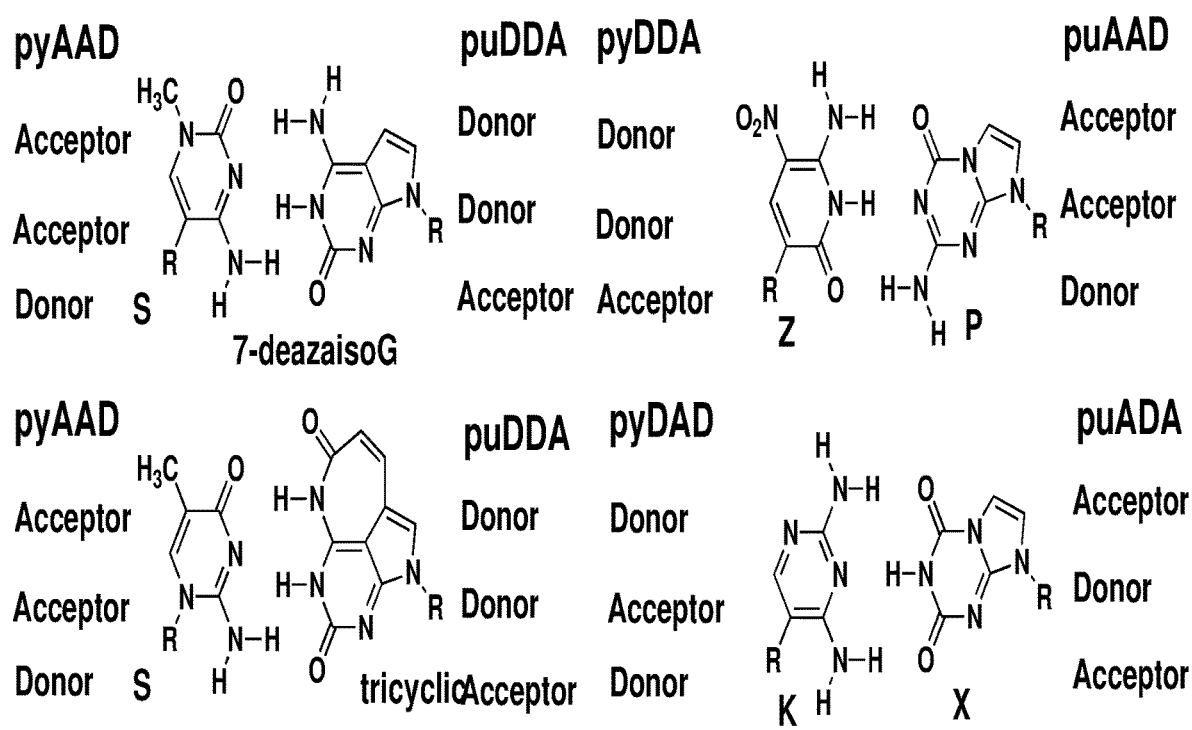
FIG. 3. The presently preferred embodiments of some of the non-standard AEGIS nucleobases and their pairs. These have a Watson-Crick geometry, with large purines or purine analogs (indicated by "pu") pairing with small pyrimidines or pyrimidine analogs (indicated by "py") joined by hydrogen bonds. The hydrogen-bonding acceptor (A) and donor (D) groups are listed from the major to the minor groove as indicated. Electron density presented to the minor groove is shown by the shaded lobes. Note that some non-standard pyrimidines do not present this density.
Figure 4:
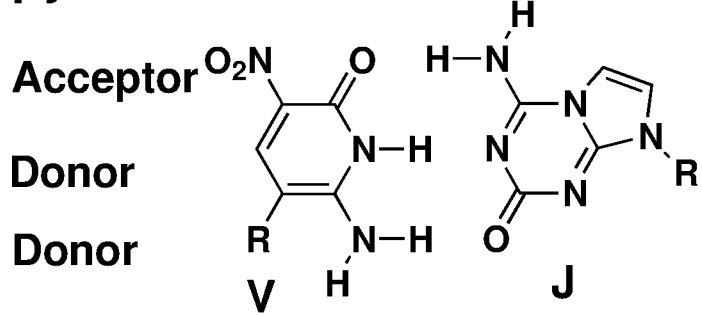
FIG. 4. The presently preferred embodiments of some of the non-standard AEGIS nucleobases and their pairs. These have a Watson-Crick geometry, with large purines or purine analogs (indicated by "pu") pairing with small pyrimidines or pyrimidine analogs (indicated by "py") joined by hydrogen bonds. The hydrogen-bonding acceptor (A) and donor (D) groups are listed from the major to the minor groove as indicated. Electron density presented to the minor groove is shown by the shaded lobes. Note that some non-standard pyrimidines do not present this density.
Figure 4:
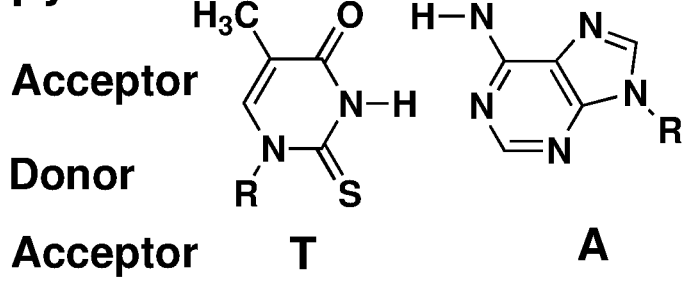
Figure 4:
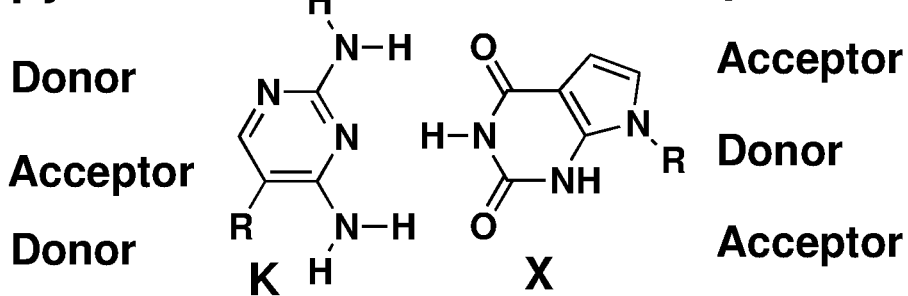
Figure 4:
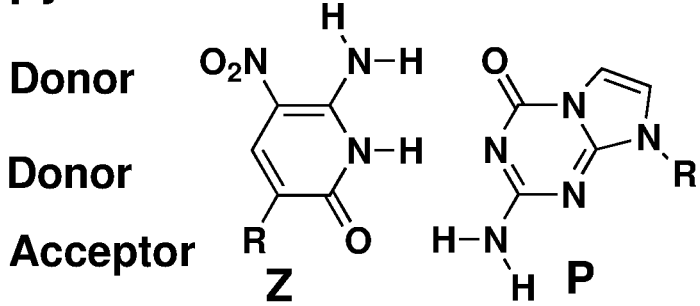
Figure 5:
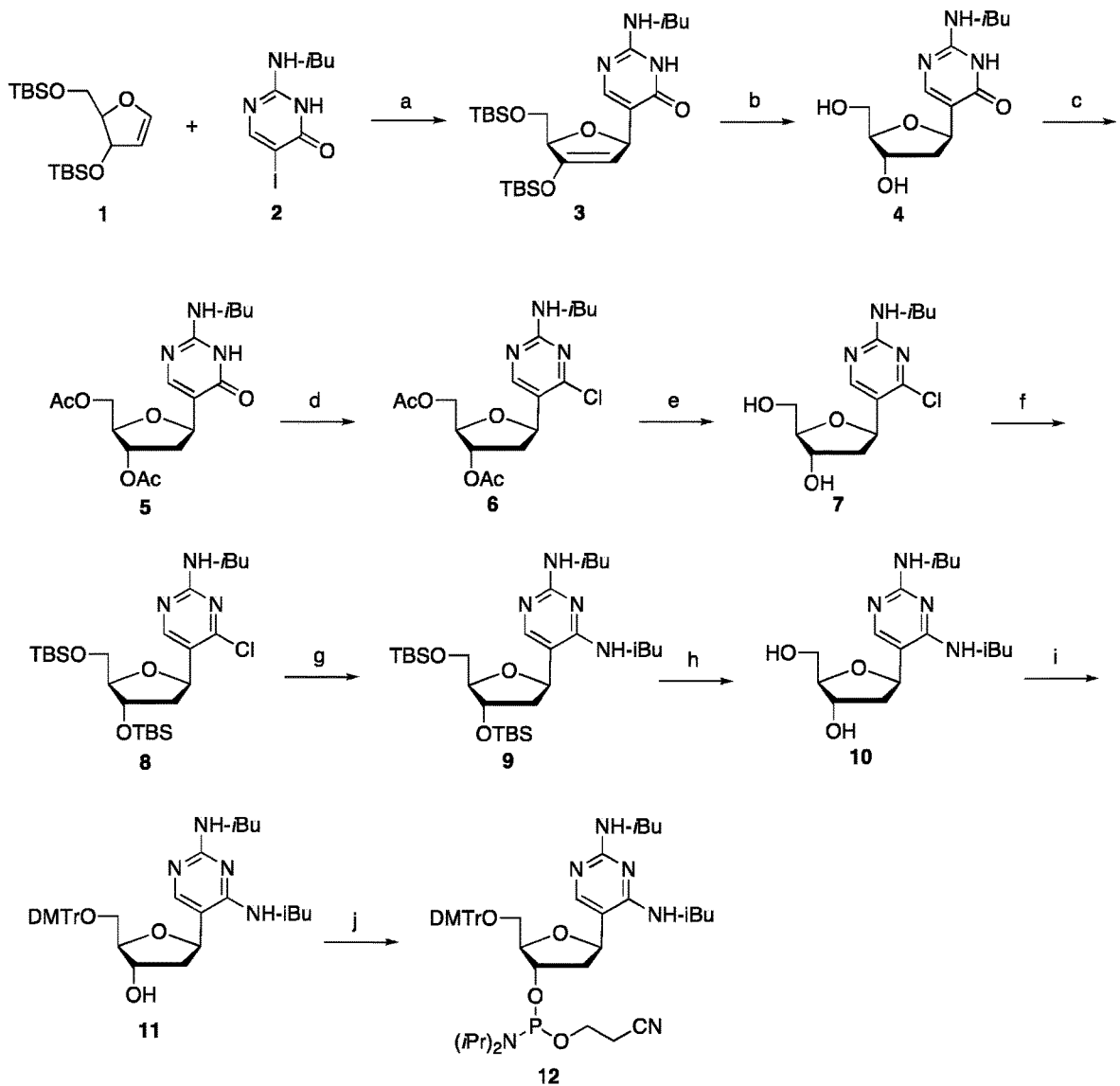
FIG. 5. Synthesis of an AEGIS component. (a) N,O-bis(trimethylsilyl)acetamide, $Pd(OAc)_2$, $AsPh_3$, N,N-diisopropylethylamine, DMF, 80° C., 20 h; (b) (i) HF-pyridine, THF, rt, 20 h, (ii) $NaBH(OAc)_3$, AcOH, MeCN, 0° C., 45 min, 52%, 3steps; (c) $Ac_2O$, pyridine, rt, 20 h, 91%; (d) $BnNEt_3Cl$, $PhNMe_2$, $POCl_3$, MeCN, reflux, 1 h, 92%; (e) 2N—NaOH, pyridine/MeOH, 0° C., 20 min, 94%; (f) TBDMSCl, imidazole, DMF, rt, 20 h, 98%; (g) $Pd_2dba_3CHCl_3$, xantphos, $Cs_2CO_3$, isobutyramide, toluene, 110° C., 1 h, 67%; (h) TBAF, THF, rt, 20 h, 79%; (i) DMTCl, pyridine, rt, 24 h, 80%; (j) 2-cyanoethyl-N,N-diisopropylchlorophosphoramidite, $(i-Pr)_2NEt$, $CH_2Cl_2$, rt, 2 h, 71%.
Figure 6:
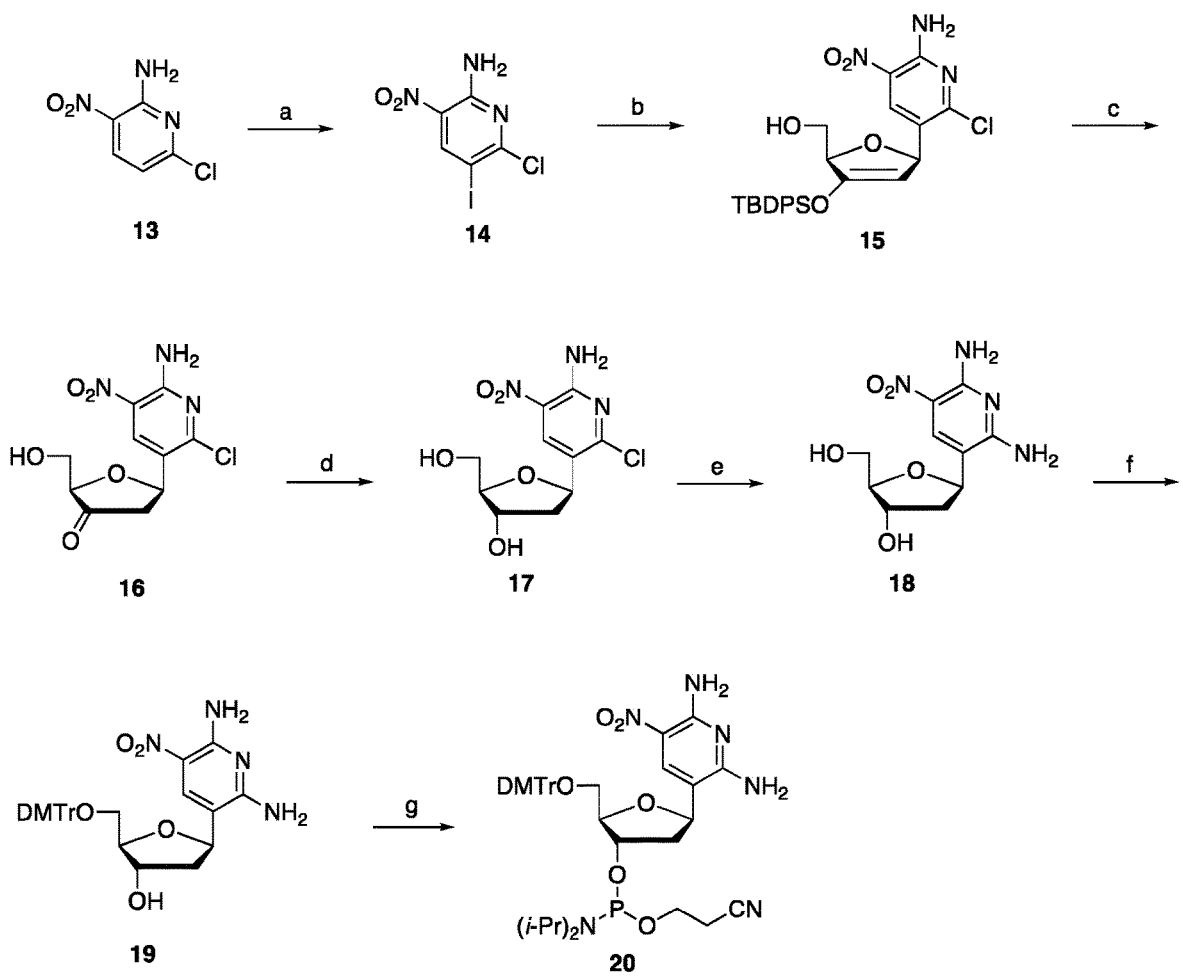
FIG. 6. Synthesis of an AEGIS component. Reagent and conditions: (a) $I_2/H_5IO_6$, $AcOH/H_2SO_4/H_2O$, 95° C., 1 h, 88%; (b) $Pd(OAc)_2$, $AsPh_3$, $Ag_2CO_3$, $CHCl_3$, reflux, 20 h, 63%; (c) TBAF, THF/AcOH, 0° C., 30 min; (d) $NaBH(OAc)_3$, MeCN/AcOH, 0° C., 1 h, 80%, 2 steps; (e) 7N—$NH_3$ in MeOH, 110° C., 20 h, 90%; (f) DMTCl, DMAP, pyridine, rt, 4 h, 62%; (g) 2-cyanoethyl-N,N-diisopropylchlorophosphoramidite, $(i-Pr)_2NEt$, $CH_2Cl_2$, rt, 30 min, 87%.
Figure 7:
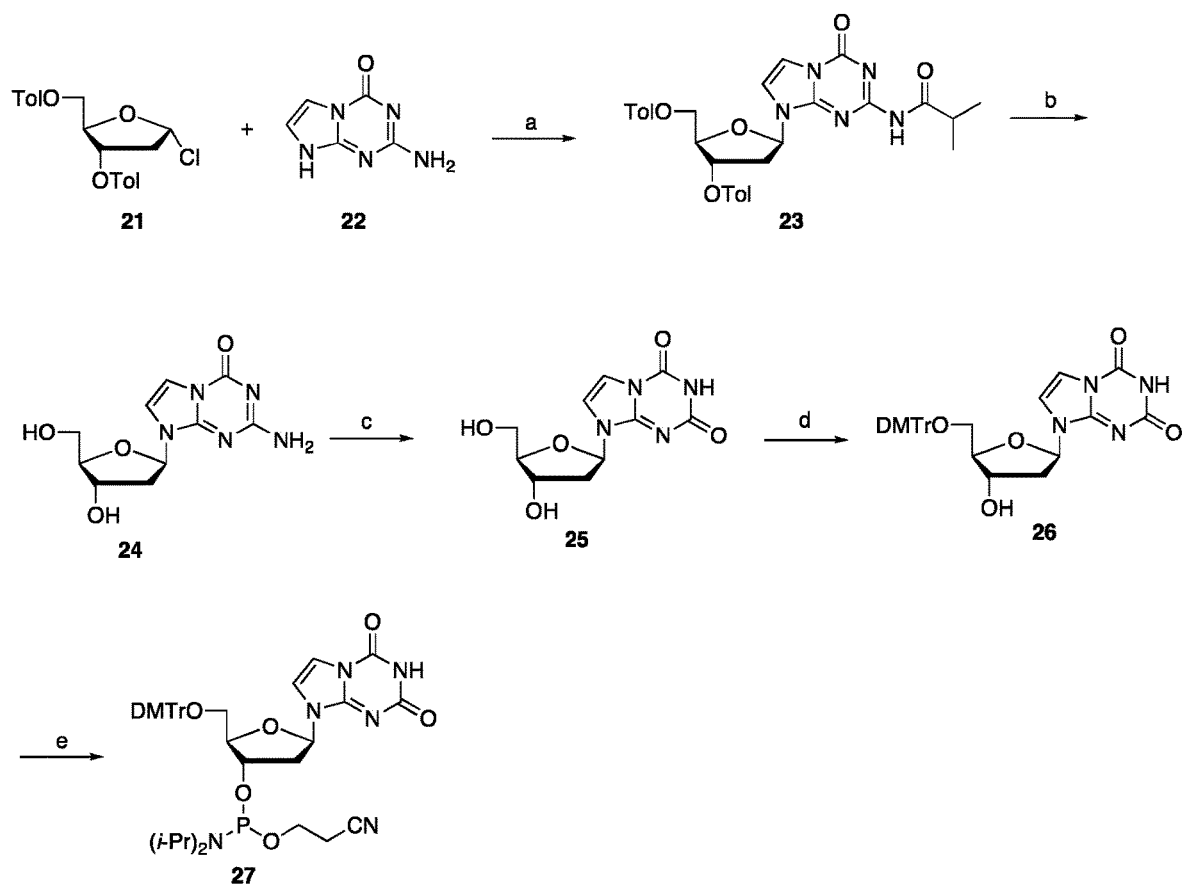
FIG. 7. Synthesis of an AEGIS component. Reagent and conditions: (a) (i) 10% aq. $K_2CO_3$, $Bu_4NHSO_4$, $CH_2Cl_2$, rt, 1 h, (ii) isobutyric anhydride, DMAP, pyridine, rt, 20 h, 19%; (b) $MeNH_2$, MeOH, rt, 2 days, 90%; (c) $NaNO_2/H_2O$, AcOH, rt, 2 days, 67%; (d) DMTCl, pyridine, rt, 20 h, 58%; (e) 2-cyanoethyl-N,N-diisopropylchlorophosphoramidite, N-Methylmorpholine, $CH_2Cl_2$, rt, 1 h, 41%.

A central teaching of this disclosure is that hydrogen-bonding pattern designated using this systematic nomenclature is distinct, in concept, from the organic molecule that is used to implement the hydrogen-bonding pattern. Which organic molecule is chosen to implement a specific hydrogen-bonding pattern determines, in large part, the utility of the non-standard hydrogen-bonding pattern, in various applications to which it might be applied.

Thus, guanosine is a nucleoside that implements the puADD hydrogen-bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups.

Likewise, isoguanosine is a nucleoside that implements the puDDA hydrogen-bonding pattern. So does, however, 7-deazaisoguanosine, 3-deazaisoguanosine, 3,7-dideazaisoguanosine, and any of any number of other purines and purine derivatives, including those that carry side chains to which are appended functional groups, such as fluorescent, fluorescent quencher, attachment, or metal complexing groups, on the exocyclic amino group or at position 7.

Likewise, xanthine is a nucleobase that implements the puADA hydrogen-bonding pattern. So does, however, imidazo[1,2-a]-1,3,5-triazine-2(8H)-4(3H)-dione, and any of any number of other purines and purine derivatives, including those that carry side chains to which are appended functional groups, such as fluorescent, fluorescent quencher, attachment, or metal complexing groups.

The presently preferred embodiments of the instant invention with respect to eight non-standard nucleotides, which form four base pairs, is now presented, with reference (and/or cross-reference) to systematic nomenclature. Numbering is based on the deoxyribonucleoside analog.

For the pyDAD hydrogen bonding pattern ("py" indicates that the heterocycle is a pyrimidine analog; contrast with "pu", which indicates a purine analog), the presently preferred embodiment is 2,4-diamino-5-(1'-beta-D-2'-deoxyribofuranosyl)-pyrimidine, also named (1R)-1,4-anhydro-2-deoxy-1-C-(2,4-diamino-5-pyrimidinyl)-D-erythropentitol, or the 2,6-diamino-3-nitro-5-(1'-beta-D-2'-deoxyribofuranosyl)-pyridine.

For the puADA hydrogen bonding pattern, the presently preferred embodiment is 8-(β-D-2'-deoxyribofuranosyl)imidazo[1,2-a]-1,3,5-triazine-2(8H)-4(3H)-dione, including those that carry side chains attached to "C7", including those to which are appended functional groups, such as fluorescent, fluorescent quencher, attachment, or metal complexing groups.

For the pyAAD hydrogen bonding pattern, the presently preferred embodiment is 2'-deoxy-5-methylisocytidine (2-amino-5-methyl-1-(1'-beta-D-2'-deoxyribofuranosyl)-4(1H)-pyrimidinone) or 2-deoxy-N-methyl-pseudocytidine.

For the puDDA hydrogen bonding pattern, the presently preferred embodiment is 6-amino-1,9-dihydro-9-(1'-beta-D-2'-deoxyribofuranosyl)-3H-7-deazapurin-2-one, including those that carry side chains attached to the exocyclic amino group or to "C7", including those to which are appended functional groups, such as fluorescent, fluorescent quencher, attachment, or metal complexing groups.

For the pyDDA hydrogen bonding pattern, the presently preferred embodiment is 6-amino-3-(2'-deoxy)-D-ribofuranosyl)-5-nitro-1H-pyridin-2-one.

For the puAAD hydrogen bonding pattern, the presently preferred embodiment is 7-amino-9-(1'-beta-D-2'-deoxyribofuranosyl)-imidazo[1,2-c]-pyrimidin-5(1H)-one, including those that carry side chains attached to "C7", including those to which are appended functional groups, such as fluorescent, fluorescent quencher, attachment, or metal complexing groups.

For the pyADD hydrogen bonding pattern, the presently preferred embodiment is 2-amino-3-(2'-deoxy)-D-ribofuranosyl)-5-nitro-1H-pyridin-6-one.

For the puDAA hydrogen bonding pattern, the presently preferred embodiment is 4-amino-8-(1'-beta-D-2'-deoxyribofuranosyl)-imidazo[1,2-a]-1,3,5-triazin-2(8H)-one, including those that carry side chains attached to the exocyclic amino group or to "C7", including those to which are appended functional groups, such as fluorescent, fluorescent quencher, attachment, or metal complexing groups.

To practice the invention, standard PCR is performed to increase the number of copies (to "amplify") of a starting oligonucleotide. PCR is performed with a thermostable polymerase, which is defined as a polymerase that is stable at temperatures up to at least 80° C., and at temperatures that allow duplex DNA to be separated. Several of the preferred polymerases, matched to preferred AEGIS components, are described in the Examples, which include standard thermostable polymerases from evolutionary Family A (e.g. Taq DNA polymerase from Family A) and from Family B (e.g. Deep Vent polymerase). These include mutant forms of various thermostable polymerases, some disclosed in the Examples, which also represent inventions.

The PCR requires dissolving the oligonucleotide to be amplified in an aqueous mixture containing a thermostable DNA polymerase in a buffer where the polymerase functions, as is known in the art. The aqueous mixture must also contain nucleoside triphosphates that are Watson-Crick complementary to all of the nucleotides in the oligonucleotide to be amplified. "Watson Crick complementary" is a term of art that requires the heterocycles in the triphosphate to be size- and hydrogen bonding-complementary, as outlined above.

The PCR mixture also must contain a first oligonucleotide primer that is "substantially complementary" to a segment at or near the 3'-end of the oligonucleotide to be amplified. "Substantially complementary" is a term of art that includes the possibility that the primer:oligonucleotide complex has a small number of mismatches; the level of mismatching must not, however, be so large as to prevent the hybridization of the primer to the oligonucleotide to be amplified. This hybridization is achieved by annealing of the primer and the oligonucleotide by lowering the temperature of the mixture, typically starting at a temperature above 80° C. where duplexes are unstable, at an appropriate rate, as is well known in the art, to a temperature where the hybrid is substantially stable. It is understood in the art, and taught here as well, that the temperatures of melting, annealing, and primer extension must be adjusted (or "preselected") to give the desired formation of single strand separation, subsequent hybridization, and polymerase-catalyze copying.

The first extension in the PCR arises by incubating the mixture of primer, oligonucleotide, polymerase, and triphosphates at a temperature where the polymerase extends the first oligonucleotide primer to give an extension product that is substantially complementary to the oligonucleotide. In the initial product, the extension product forms a duplex with said oligonucleotide. Further, the extension product, when it is separated from said oligonucleotide, can hybridize to a second oligonucleotide primer, which that a sequence substantially identical to a portion of said oligonucleotide at or near its 5'-end, and is therefore substantially complementary to the extension product at its 3'-end. This primer extension time is variable, as is known in the art, but preferably is between 30 seconds and three minutes.

For the process to continue, the temperature of the mixture is then increased to a temperature sufficient to separate the initial oligonucleotide from its extension product. This gives both primers a chance to bind upon subsequent annealing, the first primer to the original oligonucleotide, and the second to the extension product. This temperature is generally above 80° C. The annealing is then achieved by lowering the temperature of the mixture to a temperature at which the primers can hybridize. Typically, the temperature is then adjusted to a temperature optimal for the polymerase to extend all primer-template complexes.

These steps are repeated an arbitrary number of times, but generally at least five times. The extent of amplification depends on the ratio of primers to original oligonucleotide. As is known in the art, unequal amounts of the two primers give "asymmetric PCR".

It is taught in this disclosure that various combinations of standard and nonstandard nucleotides may be selected to have utility in user-chosen applications. It is convenient to consider these in three sections.

First, if the oligonucleotide being amplified contains a purine analog implementing a donor-donor-acceptor hydrogen bonding pattern, retention of the information encoded by that analog must address possible tautomerization to form a minor tautomer that complement thymidine or uridine. Accordingly, this disclosure teaches the preferred use of 2'-deoxy-7-deazaisoguanosine or its tricyclic analog, not isoguanosine, and 2'-thiothymidine triphosphate, not thymidine triphosphate, in the amplification. Further, if the amplification involves a pyrimidine analog implementing an acceptor-acceptor-donor hydrogen bonding pattern, retention of the information encoded by that analog must address the instability of the N-glycosidic bond of isocytidine. Accordingly, this disclosure teaches the preferred use of 2'-deoxypseudocytidine.

Next, if the oligonucleotide being amplified contains a purine analog implementing a donor-acceptor-acceptor hydrogen bonding pattern, retention of the information requires a pyrimidine analog to implement the complementary acceptor-donor-donor hydrogen bonding pattern that does not rapidly epimerize. Accordingly, in this case for this purpose, this disclosure teaches the preferred use of a nitroaminopyrimidinone heterocycle.

Third, if the oligonucleotide being amplified contains a purine analog implementing an acceptor-donor-acceptor hydrogen bonding pattern, retention of the information encoded by that analog must address possible ionization of the heterocycle implementing this pattern. Accordingly, this disclosure teaches the preferred use of 2'-deoxy-7-deazaxanthosine, with the complement being a diaminopyrimidine or a diaminonitropyridine heterocycle.

EXAMPLES

Example 1

$N^4$-isobutyroyl-2'-deoxypseudoisocytosine (4)

N-isobutyroyl-isocytosine 2 (15.8 g, 51.5 mmol) was suspended in DMF (150 mL) and N,O-bis(trimethylsilyl) acetamide (24.7 mL, 101.0 mmol) was added, This mixture was stirred at room temperature for 1 h. In a separate flask, a mixture of Pd(OAc)$_2$ (1.55 g, 6.9 mmol) and AsPh$_3$ (4.22 g, 13.8 mmol) in DMF (200 mL) was stirred at room temperature for 30 min. To the first solution were added N,N-diisopropylethylamine (19.3 mL, 110.8 mmol) and a solution of glycal 1 (11.8 g, 34.2 mmol) in DMF (50 mL), followed by addition of Pd catalyst solution at room temperature. The reaction mixture was stirred at 80° C. for 20 h, cooled to room temperature and concentrated. The residue was diluted with EtOAc and filtered through a celite pad. The filtrated was concentrated and the residue was purified by silica gel column chromatography (Hex/EtOAc=2/1 to 1/2) to give compound 3. This was dissolved in THF (300 mL) and a solution of HF-pyridine (70%, 7.7 mL) in THF (100 mL) was added at room temperature. After 1 h, additional HF-pyridine (2.1 mL) was added. The reaction mixture was stirred at room temperature for 20 h and concentrated. The residue was purified by silica gel column chromatography (CH$_2$Cl$_2$/MeOH=10/1) to give the ketone derivative, which was dissolved in CH$_3$CN/AcOH (2/1, 210 mL). This solution was cooled to 0° C. and NaBH(OAc)$_3$ (5.4 g, 25.5 mmol). The reaction mixture was stirred at 0° C. for 30 min and acetone (10 mL) was added. The solvent was removed to dryness and the residue was purified by silica gel column chromatography (CH$_2$Cl$_2$/MeOH=10/1 to 7/1) to give 4 (5.25 g, 17.7 mmol, 52%) as a white solid.

$^1$H NMR (DMSO-d$_6$, 300 MHz) δ 11.98, 11.58 (2brs, 2H), 7.85 (s, 1H), 4.98 (d, J=3.9, 1H), 4.87 (m, 1H), 4.75 (m, 1H), 4.11 (m, 1H), 3.71 (m, 1H), 3.38 (m, 2H), 2.65 (m, 1H), 2.04 (m, 1H), 1.73 (m, 1H), 1.08, 1.06 (2s, 6H); $^{13}$C NMR (DMSO-d$_6$, 75 MHz) δ 180.7, 172.7, 151.1, 123.4, 87.9, 74.5, 72.9, 63.0, 41.3, 40.9, 35.3, 19.5.

$N^4$-isobutyroyl-3',5'-di-O-acetyl-2'-deoxypseudoisocytosine (5)

To a stirred solution of 4 (5.25 g, 17.7 mmol) in pyridine (100 mL) was added Ac$_2$O (5 mL, 53.1 mmol) at room temperature. After being stirred at room temperature for 20 h, the reaction mixture was concentrated and the residue was purified by silica gel column chromatography (Hex/EtOAc=1/4 to EtOAc) to give 5 (6.15 g, 16.1 mmol, 91%) as a white foam.

$^1$H NMR (DMSO-d$_6$, 300 MHz) δ 11.99, 11.61 (2brs, 2H), 7.78 (s, 1H), 5.11 (d, J=5.1, 1H), 4.89 (m, 1H), 4.21 (m, 1H), 4.08 (m, 2H), 2.67 (m, 1H), 2.28 (m, 1H), 2.14 (m, 1H), 2.96, 2.01 (2s, 6H), 1.10, 1.08 (2s, 6H); $^{13}$C NMR (DMSO-d$_6$, 75 MHz) δ 180.8, 170.9, 151.4, 122.0, 82.2, 76.8, 74.9, 64.5, 41.0, 39.4, 35.4, 21.6, 21.3, 19.5.

2-Isobutyroylamino-4-chloro-5-(1'-β-3',5'-di-O-acetyl-D-2'-deoxyribofuranosyl)-pyrimidine (6)

A mixture of 5 (5.4 g, 14.2 mmol), BnNEt$_3$Cl (6.48 g, 28.4 mmol), PhNMe$_2$ (3.6 mL, 28.4 mmol) and POCl$_3$ (7.95 mL, 85.3 mmol) in CH$_3$CN (130 mL) was refluxed for 1 h, cooled to room temperature and concentrated. The residue was diluted with EtOAc and washed with sat. aqueous NaHCO$_3$ solution. The organic layer was dried (Na$_2$SO$_4$), filtered and concentrated. The residue was purified by silica gel column chromatography (Hex/EtOAc=1/3) to give 6 (5.5 g, 13.8 mmol, 92%) as a white foam.

$^1$H NMR (CDCl$_3$, 300 MHz) δ 8.70 (s, 1H), 8.48 (s, 1H), 5.21-5.30 (m, 2H), 4.35 (m, 1H), 4.26 (m, 2H), 2.98 (m, 1H), 2.56 (m, 1H), 2.12, 2.03 (2s, 6H), 1.90 (m, 1H), 1.25, 1.23 (2s, 6H); $^{13}$C NMR (CDCl$_3$, 75 MHz) δ 176.3, 170.8, 159.1, 157.5, 156.7, 127.6, 83.0, 76.3, 75.7, 64.3, 39.7, 36.1, 21.3, 21.1, 19.3.

2-Isobutyroylamino-4-chloro-5-(1'-β-D-2'-deoxyribofuranosyl)-pyrimidine (7)

To a cooled solution 6 (5.5 g, 13.8 mmol) in pyridine/MeOH (140 mL/21 mL) was added 2N—NaOH (13.8 mL)

at 0° C. After 20 min at 0° C., the reaction mixture was neutralized with Dowex 50WX8-200 resin. The resin was filtered and washed with H$_2$O/pyridine (4/1, 200 mL). The filtrated was concentrated and the residue was purified by silica gel column chromatography (CH$_2$Cl$_2$/MeOH=9/1) to give 7 (4.1 g, 13.0 mmol, 94%) as a white solid.

$^1$H NMR (DMSO-d$_6$, 300 MHz) δ 10.76 (s, 1H), 8.74 (s, 1H), 5.28 (m, 1H), 5.13 (m, 1H), 4.95 (m, 1H), 4.18 (m, 1H), 3.81 (m, 1H), 3.47 (m, 2H), 2.69 (m, 1H), 2.19 (m, 1H), 1.73 (m, 1H), 1.05, 1.02 (2s, 6H).

2-Isobutyroylamino-4-chloro-5-(1'-β-3',5'-di-O-(tert-butyldimethylsilyl)-D-2'-deoxyribofuranosyl)-pyrimidine (8)

To a stirred solution of 7 (2.5 g, 7.9 mmol) in DMF (80 mL) were added TBDMSCl (2.98 g, 19.8 mmol) and imidazole (2.15 g, 31.6 mmol) at room temperature. After 20 h, the reaction mixture was diluted with ethyl ether and washed with water. The organic layer was dried (Na$_2$SO$_4$), filtered and concentrated. The residue was purified by silica gel column chromatography (Hex/EtOAc=4/1) to give 8 (4.23 g, 7.8 mmol, 98%) as a white foam.

$^1$H NMR (CDCl$_3$, 300 MHz) δ 8.75 (s, 1H), 8.37 (s, 1H), 5.29 (dd, J=3.3, 9.9, 1H), 4.39 (m, 1H), 3.97 (m, 1H), 3.73 (dd, J=3.3, 10.8, 1H), 3.60 (dd, J=5.1, 10.5, 1H), 3.00 (m, 1H), 2.33 (m, 1H), 1.69 (m, 1H), 1.25, 1.22 (2s, 6H), 0.90, 0.87 (2s, 18H), 0.08, 0.06 (2s, 6H); $^{13}$C NMR (CDCl$_3$, 75 MHz) δ 176.4, 158.9, 157.7, 156.3, 129.3, 88.2, 75.1, 74.0, 63.6, 42.4, 35.9, 26.1, 25.9, 19.3, 18.5, 18.2.

2,4-Bis(isobutyroylamino)-5-(1'-β-3',5'-di-O-(tert-butyldimethylsilyl)-D-2'-deoxyribofuranosyl)-pyrimidine (9)

A reaction flask was charged with 8 (4.23 g, 7.8 mmol), Pd$_2$dba$_3$-CHCl$_3$ (201 mg, 0.2 mmol), Xantphos (337 mg, 0.6 mmol), Cs$_2$CO$_3$ (3.55 g, 10.9 mmol) and isobutyramide (745 mg, 8.6 mmol) and purged with argon. Anhydrous toluene (50 mL) was added to this mixture. The reaction mixture was stirred at 110° C. for 1 h, cooled to room temperature, diluted with CH$_e$Cl$_2$ and filtered through a celite pad. The filtrated was concentrated and the residue was purified by silica gel column chromatography (Hex/EtOAc=2/1) to give 9 (3.1 g, 5.2 mmol, 67%) as a pale yellow foam.

$^1$H NMR (CDCl$_3$, 300 MHz) δ 9.40 (s, 1H), 8.45 (s, 1H), 8.31 (s, 1H), 5.08 (dd, J=4.8, 10.8, 1H), 4.39 (m, 1H), 4.00 (m, 1H), 3.68 (dd, J=3.9, 10.8, 1H), 3.55 (dd, J=5.1, 11.1, 1H), 2.88 (m, 1H), 2.78 (m, 1H), 2.17 (m, 1H), 2.10 (m, 1H), 1.22 (m, 12H), 0.90, 0.85 (2s, 18H), 0.10, 0.03, 0.01 (3s, 12H); $^{13}$C NMR (CDCl$_3$, 75 MHz) δ 176.1, 157.4, 156.7, 156.6, 116.3, 88.9, 76.0, 73.6, 63.7, 40.7, 36.8, 36.2, 26.0, 25.9, 19.5, 19.4, 19.2, 18.5, 18.2.

2,4-Bis(isobutyroylamino)-5-(1'-β-D-2'-deoxyribofuranosyl)-pyrimidine (10)

To a stirred solution of 9 (3.1 g, 5.2 mmol) in THF (60 mL) was added 1M TBAF in THF (13.5 mL) at room temperature. After being stirred at room temperature for 20 h, the reaction mixture was concentrated and the residue was purified by silica gel column chromatography (CH$_2$Cl$_2$/MeOH=9/1 to 7/1) to give 10 (1.5 g, 4.1 mmol, 79%) as a white solid.

$^1$H NMR (DMSO-d$_6$, 300 MHz) δ 10.42 (s, 1H), 9.99 (s, 1H), 8.62 (s, 1H), 5.17 (d, J=3.6, 1H), 4.96 (m, 1H), 4.16 (m, 1H), 3.69 (m, 1H), 3.47 (m, 2H), 2.77 (m, 2H), 2.06 (m, 1H), 1.74 (m, 1H), 1.01-1.08 (m, 12H). $^{13}$C NMR (DMSO-d$_6$, 75 MHz) δ 176.9, 176.2, 158.6, 157.1, 156.5, 122.9, 88.1, 75.0, 72.6, 62.4, 41.9, 40.6, 39.0, 35.0, 34.9, 19.9, 19.8, 19.6.

2,4-Bis(isobutyroylamino)-5-(1'-β-5'-O-(4,4'-dimethoxytriphenylmethyl)-D-2'-deoxyribofuranosyl)-pyrimidine (11)

To a stirred solution of 10 (1.5 g, 4.1 mmol) in pyridine (50 mL) was added DMTCl (2.08 g, 6.1 mmol) at room temperature. The reaction mixture was stirred at room temperature for 24 h, quenched with MeOH (15 mL) and concentrated. The residue was purified by neutral silica gel column chromatography (Hex/Acetone=2/3) to give 11 (2.2 g, 3.3 mmol, 80%) as a white foam.

$^1$H NMR (CDCl$_3$, 300 MHz) δ 9.56 (s, 1H), 8.92 (s, 1H), 8.31 (s, 1H), 7.15-7.34 (m, 9H), 6.74 (d, J=5.7, 4H), 5.19 (dd, J=4.5, 7.5, 1H), 4.45 (m, 1H), 4.22 (m, 1H), 3.75 (s, 6H), 3.22 (m, 2H), 2.82 (m, 1H), 2.46 (m, 1H), 2.39 (m, 1H), 2.16 (m, 1H), 1.06-1.21 (m, 12H); $^{13}$C NMR (CDCl$_3$, 75 MHz) δ 175.7, 158.7, 157.4, 156.9, 156.4, 149.9, 144.7, 135.3, 135.8, 130.1, 129.3, 128.2, 128.0, 124.0, 115.9, 113.3, 87.3, 86.5, 75.9, 73.4, 64.6, 55.4, 40.3, 37.2, 36.5, 19.3.

1β-[2,4-Bis(isobutyroylamino)pyrimidin-5-yl]-5-O-(4,4'-dimethoxytriphenylmethyl)-D-2-deoxyribofuranose-3-[(2-cyanoethyl)(N,N-diisopropyl)]phosphoramidite (12)

To a stirred solution of 11 (1.55 g, 2.32 mmol) in CH$_2$Cl$_2$ (50 mL) were added N,N-diisopropylethylamine (0.81 mL, 4.7 mmol) and 2-cyanoethyl-N,N-diisopropylchlorophosphoramidite (0.67 mL, 3.0 mmol) at room temperature. After 2 h, the reaction mixture was concentrated and the residue was purified by neutral silica gel column chromatography (Hex/Acetone=2/3) to give 12 (1.42 g, 1.65 mmol, 71%) as a white foam.

$^1$H NMR (CDCl$_3$, 300 MHz) δ 9.35, 9.40 (2s, 1H), 8.49, 8.51 (2s, 1H), 8.32, 8.34 (2s, 1H), 7.23-7.37 (m, 9H), 6.75 (m, 4H), 5.12 (m, 1H), 4.78 (m, 1H), 4.26 (m, 1H), 3.52-3.83 (m, 10H), 3.17-3.27 (m, 2H), 2.91 (m, 1H), 2.50-2.67 (m, 2H), 2.41 (t, J=6.0, 1H), 2.17 (m, 1H), 1.03-1.26 (m, 24H); $^{31}$P-NMR (120 MHz, CDCl$_3$): δ 149.9, 149.4.

Example 2

2-Amino-6-chloro-5-iodo-3-nitropyridine (14)

A mixture of 2-amino-6-chloro-3-nitropyridine 13(5.7 g, 32.8 mmol), water (4.5 mL), c-H$_2$SO$_4$ (1.26 mL) and H$_5$IO$_6$ (1.59 g) was stirred for 15 min at 95° C. Iodine (3.6 g) was added in portions. The reaction mixture was stirred for 1 h at 95° C., cooled to room temperature, poured into sat. aqueous sodium thiosulfate solution and extracted with ethyl acetate. The organic layer was dried (Na$_2$SO$_4$), filtered and concentrated. The residue was purified by silica gel column chromatography (Hex/EtOAc=3/2) to give compound 14 (8.7 g, 29.1 mmol, 88%).

$^1$H NMR (DMSO-d$_6$, 300 MHz) δ 8.62 (s, 1H), 8.26 (brs, 2H)

2-Amino-6-chloro-5-[1'-β-3'-O-(tert-butyldiphneylilyl)-D-2'-deoxy-erythro-pent-2-enofuranosyl]-3-nitropyridine (15)

A solution of palladium acetate (187 mg, 0.83 mmol) and triphenyl arsine (509 mg, 1.66 mmol) in chloroform (30 mL)

was stirred for 30 min at room temperature. This solution was added to the mixture of glycal (3.25 g, 9.2 mmol), 7 (2.49 g, 8.3 mmol) and silver carbonate (4.59 g, 16.6 mmol) in chloroform (60 mL) at room temperature. The reaction mixture was refluxed overnight, cooled to room temperature and filtered through a celite pad, the filtrate was concentrated and the residue was purified by silica gel column chromatography (Hex/EtOAc=4/1 to 7/3) to give compound 15 (2.75 g, 5.23 mmol, 63%) as an orange foam.

$^1$H NMR (CDCl$_3$, 300 MHz) δ 8.42 (s, 1H), 7.73-7.82 (m, 4H), 7.41-7.48 (m, 6H), 5.83 (m, 1H), 7.77 (m, 1H), 4.23 (s, 1H), 3.90 (m, 2H), 1.78 (t, J=6.0, 1H), 1.23 (t, J=6.9, 1H), 1.08 (s, 9H).

2-Amino-6-chloro-3-nitro-5-(1'-β-D-2'-deoxyribofuranosyl)-pyridine (17)

To a stirred solution of 15 (2.75 g, 5.23 mmol) in THF (60 mL) as added AcOH (1.5 mL), followed by addition of 1M TBAF in THF (7.9 mL) at 0° C. After 30 min stirring, the reaction mixture was concentrated to give crude compound 16, which was dissolved in CH$_3$CN/AcOH (46 mL/23 mL). To this mixture was added Na(OAc)$_3$BH (1.66 g, 7.83 mmol) at 0° C. After 1 h stirring at 0° C., acetone was added and the reaction mixture was concentrated. The residue was purified by silica gel column chromatography (CH$_2$Cl$_2$/MeOH=15/1) to give compound 17 (1.21 g, 4.18 mmol, 80%) as a yellow solid.

$^1$H NMR (DMSO-d$_6$, 300 MHz) δ 8.49 (s, 1H), 8.14 (brs, 2H), 5.13 (d, 1H, J=3.9), 5.06 (dd, J=5.7, 9.9, 1H), 4.83 (t, J=5.4, 1H), 4.17 (m, 1H), 3.78 (m, 1H), 3.43-3.52 (m, 2H), 2.16 (dd, J=5.7, 12.6, 1H), 1.66 (m, 1H).

2,6-Di-amino-3-nitro-5-(1'-β-D-2'-deoxyribofuranosyl)-pyridine (18)

Compound 17 (1.2 g, 4.14 mmol) was dissolved in 7N NH$_3$ in MeOH (80 mL) and heated overnight at 110° C. The reaction mixture cooled to room temperature and concentrated. The resulting solid was washed with ethanol/ether mixture to give compound 18 (1 g, 3.7 mmol, 90%) as a yellow solid.

$^1$H NMR (DMSO-d$_6$, 300 MHz) δ 7.96 (s, 1H), 7.25 (brs, 4H), 5.01-5.15 (m, 2H), 4.88 (dd, J=6.3, 9.6, 1H), 4.20 (m, 1H), 3.74 (m, 1H), 3.47-3.58 (m, 2H), 1.89-1.97 (m, 2H); $^{13}$C NMR (DMSO-d$_6$, 75 MHz) δ 160.6, 155.4, 133.7, 118.2, 112.7, 88.4, 78.1, 72.7, 62.1, 40.9; $^{31}$P-NMR (120 MHz, CDCl$_3$): δ 149.9, 149.4.

2,6-Di-amino-3-nitro-5-(1'-β-5'-O-(4,4'-dimethoxytriphenylmethyl)-D-2'-deoxyribofuranosyl)-pyridine (19)

To a stirred solution of 18 (310 mg, 1.15 mmol) in pyridine (20 mL) was added DMTCl (428 mg, 1.26 mmol) at room temperature. After being stirred at room temperature for 3 h, catalytic amount of DMAP was added. The reaction mixture was stirred for additional 1 h and concentrated. The residue was purified by silica gel column chromatography (Hex/EtOAc=1/2 to 1/4) to give compound 19 (410 mg, 0.72 mmol, 62%) as a yellow foam.

$^1$H-NMR (300 MHz, DMSO-d$_6$): δ 8.07 (s, 1H), 6.79-8.0 (m, 17H), 5.13 (d, J=3.9, 1H), 4.94 (dd, J=9.0, 6.0, 1H), 4.11 (m, 1H), 3.85 (m, 1H), 3.71 (s, 6H), 3.08 (d, J=3.6, 2H), 2.15 (m, 1H), 1.86 (m, 1H).

1β-[2,6-Di-amino-3-nitro-pyridin-5-yl]-5-O-(4,4'-dimethoxytriphenylmethyl)-D-2-deoxyribofuranose-3-[(2-cyanoethyl)(N,N-diisopropyl)]phosphoramidite (20)

To a stirred solution of compound 19 (2.23 g, 3.9 mmol) in CH$_2$Cl$_2$ (80 mL) were added N,N-diisopropylethylamine (1.02 mL, 5.86 mmol) and 2-Cyanoethyl N,N-diisopropylchloro phosphoramidite (1.13 mL, 5.1 mmol) at room temperature. The reaction mixture was stirred at room temperature for 30 min and extracted with water. The organic layer was dried (Na$_2$SO$_4$), filtered and concentrated. The residue was purified by neutral silica gel column chromatography (Hex?EtOAc=1/4) to give compound 20 (2.62 g, 3.4 mmol, 87%) as a yellow foam.

$^1$H-NMR (300 MHz, CDCl$_3$): δ 8.10, 8.08 (2s, 1H), 6.80-7.35 (m, 13H), 5.00 (m, 1H), 4.70 (m, 1H), 4.11 (m, 2H), 3.79 (s, 6H), 3.36-3.67 (m, 5H), 2.62 (m, 1H), 2.42-2.56 (m, 2H), 2.05-2.29 (, 1H), 1.05-1.28 (m, 12H); $^{31}$P-NMR (120 MHz, CDCl$_3$): δ 149.8, 149.3.

Example 3

2-Isobutylamido-8-[1'-β-3',5'-di-O-(p-toluoyl)-D-2'-deoxyribifuranosyl]-imidazo[1,2-a]-1,3,5-triazine-4-(8H)-one (23)

5-Aza-7-deazaguanine 22 (8 g, 51.9 mmol) was dissolved in 10% aqueous K$_2$CO$_3$ solution (40 g K$_2$CO$_3$ in 400 mL H$_2$O) and a solution of Bu$_4$NHSO$_4$ (1.28 g, 3.77 mmol) in CH$_2$Cl$_2$ (280 mL) at room temperature. After vigorous stirring for more than 1 min, a solution of chlorosugar 21 (21.4 g, 55.0 mmol) in CH$_2$Cl$_2$ (180 mL) at room temperature. The reaction mixture was stirred for 1 h at room temperature and the organic layer was separated. The aqueous layer was extracted with CH$_2$Cl$_2$ (500 mL×2). The combined organic layer was dried (Na$_2$SO$_4$), filtered and concentrated. The residue was dissolved in pyridine (300 mL) and DMAP (1.12 g) and isobutyric anhydride (6 mL) were added at room temperature. After stirring overnight at room temperature. The reaction mixture was concentrated and the residue was dissolved in hot MeOH (150 mL). This mixture was stored at 0° C. for 3 h and the resulting precipitate was filtered and washed with cold MeOH (50 mL) to give the β-isomer 23 (5.9 g, 10.3 mmol, 19%) as a white solid.

$^1$H NMR (DMSO-d$_6$, 300 MHz) δ 10.39 (s, 1H), 7.90 (d, J=8.1, 2H), 7.81 (d, J=8.1, 2H), 7.70 (d, J=2.7, 1H), 7.60 (d, J=2.4, 1H), 7.34 (d, J=8.1, 2H), 7.26 (d, J=8.1, 2H), 6.36 (t, J=6.6, 1H), 5.74 (m, 1H), 4.50-4.64 (m, 3H), 3.13 (m, 1H), 2.81 (m, 1H), 2.68 (m, 1H), 2.38, 2.34 (2s, 6H), 1.03, 1.01 (2s, 6H).

2-Amino-8-(1'-β-D-2'-deoxyribofuranosyl)-imidazo[1,2-a]-1,3,5-triazine-4-(8H)-one (24)

A suspension of compound 23 (5 g, 8.7 mmol) in MeOH (80 mL) was added 40% methylamine solution (5 mL) and stirred for 2 days at room temperature. After removal of solvent, ethanol/ether mixture was added to the residue. The resulting precipitate was filtered and dried to give dP nucleoside 24 (2.1 g, 7.9 mmol, 90%) as a white solid.

$^1$H NMR (DMSO-d$_6$, 300 MHz) δ 7.42 (d, J=2.4, 1H), 7.34 (d, J=2.4, 1H), 6.93 (brs, 2H), 6.13 (t, J=6.6, 1H), 5.30 (brs, 1H), 4.98 (m, 1H), 4.29 (m, 1H), 3.78 (m, 1H), 3.50 (m, 2H), 2.32 (m, 1H), 2.12 (m, 1H).

8-(1'-β-D-2'-deoxyribofuranosyl)imidazo[1,2-a]-1,3,5-triazine-2(8H)-4(3H)-dione (25)

Compound 24 (1.34 g, 5 mmol) was dissolved in acetic acid (38 mL) and a solution of NaNO₂ (2 g) in H₂O (6 mL) was added at room temperature. The reaction mixture was stirred at room temperature for 2 days and concentrated. The residue was purified by silica gel column chromatography (CH₂Cl₂/MeOH=8/1 to 4/1) to give 25 (900 mg, 3.36 mmol, 67%) as a white solid.

$^1$H NMR (DMSO-d$_6$, 300 MHz) δ 7.45 (d, 1H, J=3.0), 7.41 (d, 1H, J=3.0), 6.05 (t, 1H, J=6.6), 4.28 (m, 1H), 3.79 (m, 1H), 3.46-3.58 (m, 2H), 2.28 (m, 1H), 2.13 (m, 1H).

8-(1'-β-5'-O-(4,4'-dimethoxytriphenylmethyl)-D-2'-deoxyribofuranosyl)imidazo[1,2-a]-1,3,5-triazine-2(8H)-4(3H)-dione (26)

To a stirred solution of 25 (468 mg, 1.75 mmol) in pyridine (25 mL) was added DMTCl (652 mg, 1.92 mmol) at room temperature. After 20 h, the reaction mixture was concentrated and the residue was purified by silica gel column chromatography (EtOAc to EtOAC/MeOH=9/1) to give 26 (580 mg, 1.02 mmol, 58%) as a white foam.

$^1$H NMR (DMSO-d$_6$, 300 MHz) δ 11.25 (s, 1H), 7.16-7.41 (m, 11H), 6.82 (dd, J=2.7, 9.0, 4H), 6.07 (t, J=6.0, 1H), 5.36 (d, J=4.8, 1H), 4.27 (m, 1H), 3.88 (m, 1H), 3.71 (s, 6H), 3.10-3.19 (m, 3H), 2.38 (m, 1H), 2.17 (m, 1H).

1β-[imidazo[1,2-a]-1,3,5-triazine-2(8H)-4(3H)-dione-8-yl]-5-O-(4,4'-dimethoxytriphenylmethyl)-D-2-deoxyribofuranose-3-[(2-cyanoethyl)(N,N-diisopropyl)]phosphoramidite (27)

To a stirred solution of 26 (2.49 g, 4.4 mmol) in CH₂Cl₂ (70 mL) were added N-methylmorpholine (0.72 mL, 6.6 mmol) and 2-Cyanoethyl N,N-diisopropylchloro phosphoramidite (1.27 mL, 5.7 mmol) at room temperature. After 1 h, the reaction mixture was extracted with sat. aqueous NaHCO₃solution. The organic layer was dried (Na₂SO₄), filtered and concentrated. The residue was purified by neutral silica gel column chromatography (CH₂Cl₂/acetone=1/1) to give 27 (1/37 g, 1.8 mmol, 41%) as a white foam.

$^1$H-NMR (300 MHz, CDCl₃): δ 6.96-7.41 (m, 11H), 6.74-6.85 (m, 4H), 6.31 (t, J=6.0, 1H), 4.71 (m, 1H), 4.11 (m, 1H), 3.83 (m, 1H), 3.78 (s, 6H), 3.34-3.72 (m, 6H), 2.60 (m, 2H), 2.51 (m, 1H), 2.42 (m, 1H), 1.07-1.32 9m, 12H); $^{31}$P-NMR (120 MHz, CDCl₃): δ 150.1, 150.0.

Example 4

Figure 8:
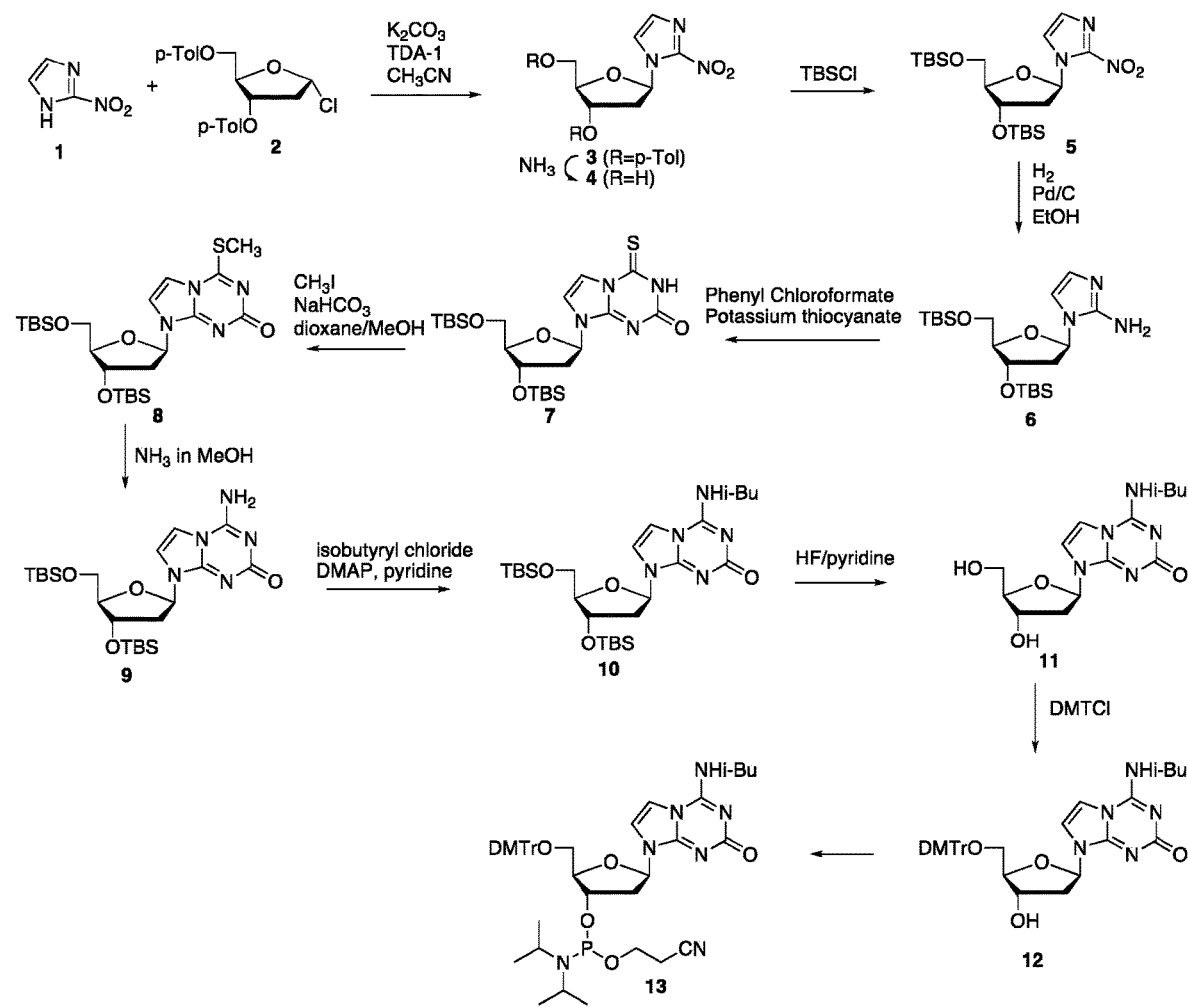
FIG. 8. Synthesis of an AEGIS component in Example 4.

The compound structure numbers make reference to FIG. 8.

Compound 4

To s stirred suspension of 2-nitroimidazole 1(2 g, 17.8 mmol), K₂CO₃ (8 g, 58 mmol) in CH₃CN (800 mL) was added TDA-1 (0.4 mL, 0.84 mmol) at RT. This mixture was stirred at RT for 1 h and chloro sugar 2(8 g, 20.7 mmol) was added at RT. After stirred at RT for 2 h, the reaction mixture was filtered and the filtrate was evaporated. The residue was purified by silica gel column chromatography (Hex/EtOAc=2/1) to give compound 3 as a white foam. To a solution of crude 3 in MeOH (150 mL) was added 40% MeNH₂ in water (10 mL) at RT. The reaction mixture was stirred overnight at RT and evaporated and ethyl ether was added to the residue. The resulting precipitate was filtered to give compound 4 (3.4 g, 14.8 mmol, 84%) as a white solid.

$^1$H NMR (300 MHz, DMSO-d$_6$): δ 8.00 (s, 1H), 7.18 (s, 1H), 6.52 (t, 1H, J=5.4 Hz), 5.29 (d, 1H, J=4.5 Hz), 5.08 (t, 1H, J=5.1 Hz), 4.23 (m, 1H), 3.83 (m, 1H), 3.55-3.66 (m, 2H), 2.42 (m, 1H), 2.28 (m, 1H). $^{13}$C NMR (75 MHz, DMSO-d$_6$): δ 144.8, 128.4, 123.9, 89.2, 88.7, 69.4, 61.0, 42.6.

Compound 5

To a stirred solution of 4 (3.4 g, 14.8 mmol) in DMF (140 mL) were added imidazole (3 g, 44.1 mmol) and TBDMSCl (6.7 g, 44.5 mmol) at RT. The reaction mixture was stirred overnight at RT, poured into water (300 mL) and extracted with ethyl ether. The organic layer was dried (Na₂SO₄), filtered and evaporated. The residue was purified by silica gel column chromatography (Hex/EtOAc=4/1) to give compound 5 (6.2 g, 13.5 mmol, 91%) as a white solid.

$^1$H NMR (300 MHz, CDCl₃): δ 7.91 (s, 1H), 7.01 (s, 1H), 6.62 (dd, 1H, J=4.2, 6.3 Hz), 4.45 (m, 1H), 3.77-3.97 (m, 3H), 2.59 (m, 1H), 2.19 (m, 1H), 0.91, 0.87 (2s, 18H), 0.11, 0.10, 0.05 (3s, 12H). $^{13}$C NMR (75 MHz, CDCl₃): δ 128.4, 122.9, 89.1, 88.2, 69.6, 61.7, 43.7, 26.1, 25.9, 18.5, 18.1.

Compound 6

A suspension of 5 (3.1 g, 6.8 mmol) and 10% Pd/C (800 mg) in EtOH (80 mL) was degassed. The reaction mixture was stirred overnight at RT under H₂, filtered through a celite pad and washed with MeOH. The filtrate was evaporated to give compound 6 (2.45 g, 5.7 mmol, 85%) as a pale yellow solid, which was used for the cyclization without further purification.

$^1$H NMR (300 MHz, DMSO-d$_6$): δ 6.68 (s, 1H), 6.38 (s, 1H), 5.84 (t, 1H, J=6.6 Hz), 5.49 (brs, 2H), 4.39 (m, 1H), 3.73 (m, 1H), 3.62 (m, 2H), 2.23 (m, 1H), 2.05 (m, 1H), 0.87, 0.086 (2s, 18H), 0.08, 0.04, 0.03 (3s, 12H). $^{13}$C NMR (75 MHz, CDCl₃): δ 149.7, 124.8, 111.4, 87.1, 83.6, 72.8, 63.5, 26.5, 26.4, 18.7, 18.5.

Compound 7

A mixture of phenyl chloroformate (0.17 mL) and potassium thiocyanate (150 mg) in EtOAc (5 mL) was stirred for 1 h at RT. To this mixture was added a solution of 6 (428 mg, 1 mmol) in 1,4-dioxane (4.5 mL) at RT. The reaction mixture was stirred for 4 h at 40° C. and MeOH (0.5 mL) was added. The mixture was evaporated and the residue was purified by silica gel column chromatography (CH₂Cl₂/acetone=10/1) to give compound 7 (165 mg, 0.32 mmol, 32%) as a yellow foam.

$^1$H NMR (300 MHz, CDCl₃): δ 9.65 (s, 1H), 7.51 (d, 1H, J=3.0 Hz), 7.43 (d, 1H, J=2.7 Hz), 6.28 (t, 1H, J=5.7 Hz), 4.45 (m, 1H), 3.88-3.96 (m, 2H), 3.75 (m, 1H), 2.35 (m, 1H), 2.21 (m, 1H), 0.93, 0.89 (2s, 18H), 0.12, 0.8 (2s, 12H). $^{13}$C NMR (75 MHz, CDCl₃): δ 171.1, 153.3, 147.4, 116.4, 110.5, 88.2, 84.8, 71.2, 62.7, 42.0, 26.2, 25.9, 18.6, 18.2.

Compound 8

Methyl Iodide (0.32 mL, 5.1 mmol) was added to a mixture of 7 (870 mg, 1.7 mmol) and NaHCO₃(214 mg, 2.04 mmol) in 1,4-dioxane (4 mL) and MeOH (8 mL). After being stirred for 30 h at RT, the reaction mixture was evaporated and the residue was purified by silica gel column chromatography (CH₂Cl₂/acetone=7/3) to give compound 8 (600 mg, 1.14 mmol, 67%) as a white foam.

$^1$H NMR (300 MHz, CDCl₃): δ 7.34 (d, 1H, J=2.7 Hz), 6.87 (d, 1H, J=2.7 Hz), 6.37 (t, 1H, J=6.0 Hz), 4.43 (m, 1H), 3.70-3.94 (m, 3H), 2.71 (s, 3H), 2.34 (m, 1H), 2.16 (m, 1H), 0.92, 0.88 (2s, 18H), 0.10, 0.06 (2s, 12H). $^{13}$C NMR (75 MHz, CDCl₃): δ 160.2, 158.6, 149.1, 116.1, 106.6, 88.0, 84.2, 71.4, 62.8, 42.0, 26.2, 25.9, 18.7, 18.2, 13.3.

Compound 9

A solution of 8 (600 mg, 1.14 mmol) in methanolic ammonia (7N, 20 mL) was stirred for 40 h at RT, evaporated and the residue was purified by silica gel column chromatography (CH$_2$Cl$_2$/MeOH=9/1) to give compound 9 (360 mg, 0.73 mmol, 64%).

$^1$H NMR (300 MHz, DMSO-d$_6$): δ 7.50-7.66 (m, 3H), 7/35 (d, 1H, J=2.4 Hz), 6/05 (t, 1H, J=6.6 Hz), 4.43 (m, 1H), 3.59-3.77 (m, 3H), 2/40 (m, 1H), 2/14 (m, 1H), 0.86, 0.85 (2s, 18H), 0.08, 0.04 (2s, 12H). $^{13}$C NMR (75 MHz, DMSO-d$_6$): δ 155.5, 152.9, 150.7, 115.3, 107.8, 87.4, 83.0, 72.5, 63.2, 39.0, 26.4, 26.3, 18.6, 18.3.

Compound 10

To a stirred solution of 9 (800 mg, 1.61 mmol) and DMAP (100 mg) in pyridine (20 mL) was added isobutyryl chloride (0.254 mL, 2.42 mmol) at RT. After being stirred for 1 h at RT, the reaction mixture was evaporated and the residue was purified by silica gel column chromatography (Hex/EtOAc=1/1) to give compound 10 (780 mg, 1.38 mmol, 85%) as a white foam.

$^1$H NMR (300 MHz, CDCl$_3$): δ 11.7 (brs, 1H), 7.37 (d, 1H, J=2.7 Hz), 7.28 (d, 1H, J=2.4 Hz), 6.30 (t, 1H, J=6.0 Hz), 4.44 (m, 1H), 3.74-3.93 (m, 3H), 2.60 (m, 1H), 2.32 (m, 1H), 2.16 (m, 1H), 1.18, 1.16 (2s, 6H), 0.92, 0.87 (2s, 18H), 0.10, 0.006 (2s, 12H). $^{13}$C NMR (75 MHz, CDCl$_3$): δ 192.5, 152.5, 149.0, 147.9, 115.9, 107.9, 88.2, 84.4, 71.4, 62.8, 42.0, 39.8, 26.2, 25.9, 19.4, 18.6, 18.2.

Compound 11

To a stirred solution of 10 (780 mg, 1.38 mmol) in THF (20 mL) was added a solution of HF (70% in pyridine, 0.95 mL) in pyridine (1.2 mL) at 0° C. After being stirred overnight at RT, the reaction mixture was evaporated and the residue was purified by silica gel column chromatography (CH$_2$Cl$_2$/MeOH=8/1) to give compound 11 (390 mg, 1.16 mmol, 84%) as a white solid.

$^1$H NMR (300 MHz, DMSO-d$_6$): δ 11.5 (s, 1H), 7.55 (d, 1H, J=2.7 Hz), 7.48 (d, 1H, J=2.7 Hz), 6.07 (t, 1H, J=6.6 Hz), 5.29 (d, 1H, J=4.2 Hz), 4.99 (t, 1H, J=5.4 Hz), 4.28 (m, 1H), 3.79 (m, 1H), 3.48-3.58 (m, 2H), 2.52 (m, 1H), 2.27 (m, 1H), 2.13 (m, 1H), 1.10, 1.08 (2s, 6H). $^{13}$C NMR (75 MHz, DMSO-d$_6$): δ 191.6, 152.3, 149.9, 148.0, 117.2, 108.9, 88.4, 83.9, 70.9, 61.9, 41.0, 39.3, 19.7.

Compound 12

To a stirred suspension of 11 (380 mg, 1.13 mmol) and DMT-Cl (460 mg, 1.36 mmol) in CH$_2$Cl$_2$ (15 mL) was added Et$_3$N (0.32 mL, 2.26 mmol) at RT. After being stirred overnight atRT, the reaction mixture was evaporated and the residue was purified by silica gel column chromatography (EtOAc to EtOAc/MeOH=9/1) to give compound 12 (620 mg, 0.97 mmol, 86%) as a pale yellow foam.

$^1$H NMR (300 MHz, CDCl$_3$): δ 11.73 (s, 1H), 6.81-7.41 (m, 11H), 6.33 (t, 1H, J=6.0 Hz), 4.67 (m, 1H), 4.13 (m, 1H), 3.79 (s, 6H), 3.42-3.52 (m, 3H), 2.57-2.68 (m, 2H), 2.43 (m, 1H), 1.19, 1.16 (2s, 6H). $^{13}$C NMR (75 MHz, CDCl$_3$): δ 192.6, 158.9, 152.8, 148.9, 147.7, 144.5, 135.6, 135.5, 130.4, 128.5, 128.2, 127.3, 116.3, 113.5, 108.1, 87.1, 86.5, 84.5, 71.6, 55.5, 41.5, 39.8, 19.4.

Compound 13

To a stirred solution of 12 (620 mg, 0.97 mmol) in CH$_2$Cl$_2$ (15 mL) were added N,N-diisopropylethylamine (0.3 mL, 1.72 mmol) and 2-Cyanoethyl N,N-diisopropylchloro-phosphoramidite (0.29 mL, 1.3 mmol) at 0° C. After being stirred for 3 h at RT, the reaction mixture was evaporated and the residue was purified by neural silica gel column chromatography (EtOAc) to give compound 13 (615 mg, 0.73 mmol, 76%) as a white foam.

$^1$H NMR (300 MHz, CDCl$_3$): δ 11.71 (s, 1H), 7.12-7.41 (m, 11H), 6.81-6.85 (m, 4H), 6.32 (t, 1H, J=6.3 Hz), 4.70 (m, 1H), 4.15 (m, 1H), 3.80 (s, 6H), 3.33-3.72 (m, 6H), 2.55-2.70 (m, 3H), 2.47 (m, 1H), 2.41 (m, 1H), 1.07-1.19 (m, 18H). $^{31}$P NMR (120 MHz, CDCl$_3$): δ 150.0, 149.9.

Synthesis of dJ-triphosphate

To a stirred solution of 12 (420 mg, 0.66 mmol) in pyridine (10 mL) was added Ac$_2$O (0.093 mL, 0.98 mmol2) at RT. The reaction mixture was stirred overnight at RT and evaporated. The residue was purified by silica gel column chromatography (EtOAc) to give compound 14 (440 mg, 0.65 mmol, 98%) as a pale yellow foam.

$^1$H NMR (300 MHz, CDCl$_3$): δ 11.72 (brs, 1H), 7.25-7.39 (m, 9H), 7.16 (d, 1H, J=2.7 Hz), 7.02 (d, 1H, J=2.7 Hz), 6.82 (d, 4H, J=8.7 Hz), 6.38 (t, 1H, J=7.2 Hz), 5.43 (m, 1H), 4.19 (m, 1H) m 3.79 (s, 6H), 3.46 (m, 2H), 2.63 (m, 1H), 2.51 (m, 2H), 2.09 (s, 3H), 1.19, 1.17 (2s, 6H). $^{13}$C NMR (75 MHz, CDCl$_3$): δ 192.5, 170.6, 158.9, 152.4, 149.6, 147.8, 144.4, 135.4, 135.3, 130.4, 128.4, 128.3, 127.4, 115.5, 113.5, 108.5, 87.3, 84.6, 83.9, 75.1, 63.7, 55.5, 39.9, 38.6, 21.2, 19.4.

A solution of 14 (440 mg, 0.65 mmol) in 3% trichloroacetic acid in CH$_2$Cl$_2$ (20 mL) was stirred for 2 h at RT and evaporated. The residue was purified by silica gel column chromatography (CH$_2$Cl$_2$/MeOH=10/1) to give compound 15 (200 mg, 0.53 mmol, 82%) as a white solid.

$^1$H NMR (300 MHz, DMSO-d$_6$): δ 9.19 (s, 1H), 7.79 (d, 1H, J=3.6 Hz), 7.13 (t, 1H, J=2.7 Hz), 6.74 (t, 1H, J=2.7 Hz), 5.97 (m, 1H) m 5.22 (m, 1H), 3.96 (m, 1H), 3.533.54 (m, 2H), 2.37-2.53 (m, 2H), 2.22 (m, 1H), 2.06 (s, 3H), 0.85 (m, 6H). $^{13}$C NMR (75 MHz, DMSO-d$_6$): δ 195.1, 176.2, 170.7, 157.7, 151.1, 114.1, 97.3, 85.5, 83.5, 75.7, 62.2, 36.9, 34.1, 21.6, 19.9.

Compound 16

To a solution of 15 (260 mg, 0.69 mmol) in pyridine (6 mL) and dioxane (4.5 mL) was added a solution of 2-chloro-4H-1,3,2-benzodioxaphosphorin-4-one (214 mg, 1.06 mmol) in dioxane (2.1 mL) at RT. After 15 min a mixture of tributylammonium pyrophosphate in DMF (0.2 M, 10.5 mL, 2.1 mmol) and tributylamine (1.14 mL, 4.8 mmol) was added. After 20 min a solution of iodine (255 mg, 1.0 mmol) and water (0.35 mL) in pyridine (18 mL) was added. After 20 min the reaction was quenched by the addition of aqueous Na$_2$SO$_3$ (5%, 1 mL). The solvents were removed in vacuo. NH$_4$OH (30 mL) was added, and the mixture was stirred overnight at RT. After evaporation, the residue was dissolve in water (50 mL) and filtered (0.2 µm). Purification by ion-exchange HPLC (Dionex BioLC DNAPac PA-100, 22×250 mm, eluent A=water, eluent B=1 M aq. NH$_4$HCO$_3$, gradient from 0 to 40% B in 20 min, flow rate=10 mL/min, Rt=12 min), followed by reverse phase HPLC (SunFires Prep C18 column, 5 µm, 19×250 mm, eluent A=25 mM TEAA pH 7, eluent B=CH$_3$CN, gradient from 0 to 20% B in 20 min, flow rate=10 mL/min, Rt=10 min) gave compound 16 as a colorless foam after lyophilization.

$^1$H NMR (300 MHz, D$_2$O): δ 7.44 (m, 1H), 7.34 (m, 1H), 6.19 (t, 1H, J=6.6 Hz), 4.56 (m, 1H), 4.01-4.07 (m, 3H), 2.38 (m, 1H), 2.32 (m, 1H). $^{31}$P NMR (120 MHz, D$_2$O): δ −9.78 (br, 1p), −10.42 (br, 1P), −22.13 (br, 1P).

Example 5

Thiothymidine is used with 7-dezazaisoguanosine and the tricyclic derivative of 7-deazaisoguanosine following a procedure used for isoguanosine itself [Sismour, A. M., Benner, S. A. (2005) The use of thymidine analogs to improve the replication of an extra DNA base pair. A synthetic biological system. *Nucl. Acids Res.* 33, 5640-5646]. This publication is which is incorporated in its entirety by reference. Reflecting the stability of the C-glycoside analog of 2'-deoxyisocytidine, known as 2'-deoxypseudocytidine, 2'-deoxypseudocytidine is the preferred partner of 7-dezazaisoguanosine and the tricyclic derivative of 7-deazaisoguanosine. Here, thymidine triphosphate must be substantially absent from the PCR mixture, where "substantially" means that it is present at less than 5% of the amount of 2'-thiothymidine triphosphate.

What is claimed is:

1. A process for increasing the number of copies of an oligonucleotide having a preselected sequence, wherein said oligonucleotide contains one or more non-standard nucleotides that carry a heterocycle selected from the group consisting of

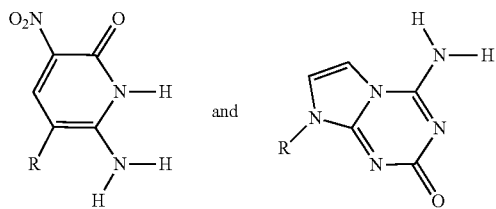

wherein R is the point of attachment of said heterocycle to the 2'-deoxyribose of said non-standard nucleotide, said process comprising:

(a) contacting said oligonucleotide in an aqueous mixture with a thermostable DNA polymerase, a first oligonucleotide primer that is sufficiently complementary to a segment at or near the 3'-end of said oligonucleotide that it hybridizes to said oligonucleotide at a preselected temperature, a second oligonucleotide primer that has a sequence substantially identical to a portion of said oligonucleotide at or near its 5'-end, and 2'-deoxynucleoside triphosphates selected from the group consisting of 2'-deoxyadenosine triphosphate, 2'-deoxyguanosine triphosphate, 2'-deoxycytidine triphosphate, thymidine triphosphate,

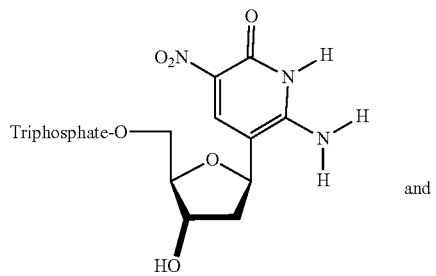

and

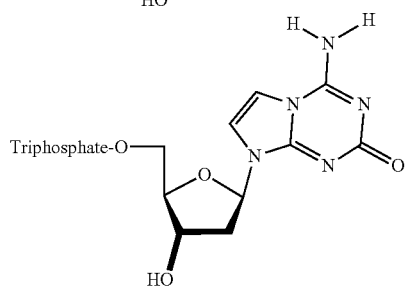

(b) incubating said mixture at said preselected temperature where said polymerase extends the first oligonucleotide primer to give an extension product that is substantially complementary to said oligonucleotide, wherein said extension product forms a duplex with said oligonucleotide, such that said extension product, when it is separated from said oligonucleotide, can hybridize with the second primer, (c) increasing the temperature of said mixture to a temperature sufficient to separate said oligonucleotide from said extension product, (d) lowering the temperature of said mixture to a preselected temperature at which the first oligonucleotide primer hybridizes to said oligonucleotide and said second oligonucleotide primer can hybridize to said extension product, and (e) repeating steps (b) through (d).

2. A process for increasing the number of copies of an oligonucleotide having a preselected sequence, wherein said oligonucleotide contains one or more non-standard nucleotides that carry a heterocycle selected from the group consisting of

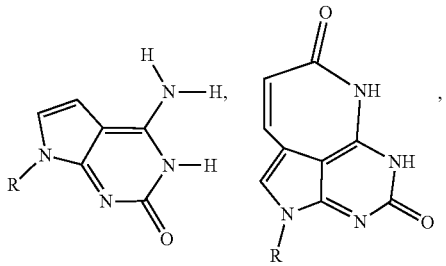

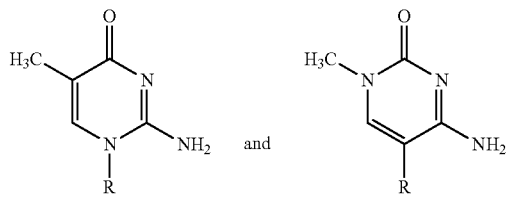

wherein R is the point of attachment of said heterocycle to the 2'-deoxyribose of said non-standard nucleotides, said process comprising:

(a) contacting said oligonucleotide in an aqueous mixture with a thermostable DNA polymerase, a first oligonucleotide primer that is sufficiently complementary to a segment at or near the 3'-end of said oligonucleotide that it hybridizes to said oligonucleotide at a preselected temperature, a second oligonucleotide primer that has a sequence substantially identical to a portion of said oligonucleotide at or near its 5'-end, and 2'-deoxynucleoside triphosphates selected from the group consisting of 2'-deoxyadenosine triphosphate, 2'-deoxyguanosine triphosphate, 2'-deoxycytidine triphosphate, 2-thiothymidine triphosphate,

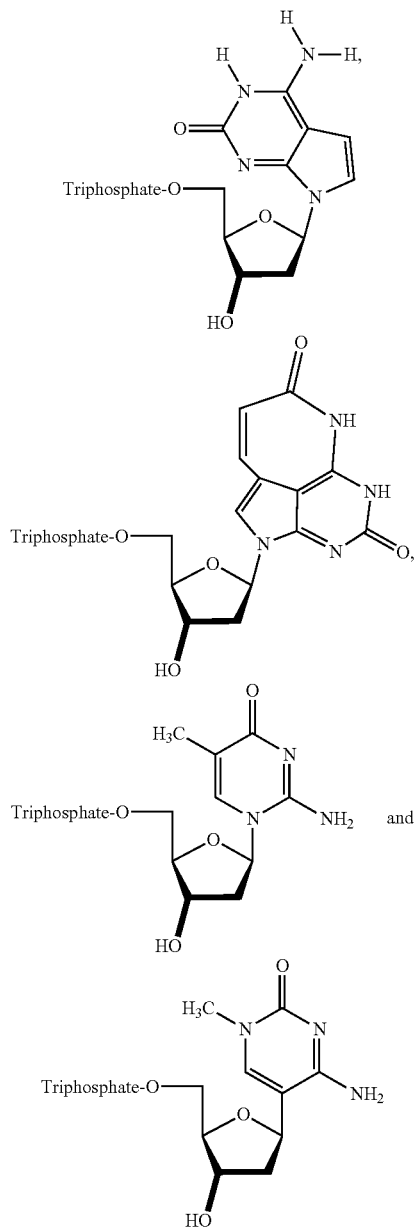

wherein said solution is substantially free of thymidine triphosphate,
(b) incubating said mixture at said preselected temperature where said polymerase extends the first oligonucleotide primer to give an extension product that is substantially complementary to said oligonucleotide, wherein said extension product forms a duplex with said oligonucleotide, such that said extension product, when it is separated from said oligonucleotide, can hybridize with the second primer,
(c) increasing the temperature of said mixture to a temperature sufficient to separate said oligonucleotide from said extension product,
(d) lowering the temperature of said mixture to a preselected temperature at which the first oligonucleotide primer hybridizes to said oligonucleotide and said second oligonucleotide primer can hybridize to said extension product, and
(e) repeating steps (b) through (d).

3. A process for increasing the number of copies of an oligonucleotide having a preselected sequence, wherein said oligonucleotide contains one or more non-standard nucleotides that carry a heterocycle selected from the group consisting of

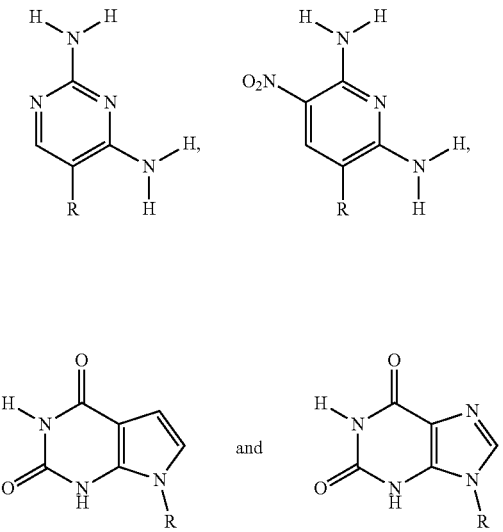

wherein R is the point of attachment of said heterocycle to the 2'-deoxyribose backbone in said non-standard nucleotides, said process comprising:
(a) contacting said oligonucleotide in an aqueous mixture with a thermostable DNA polymerase, a first oligonucleotide primer that is sufficiently complementary to a segment at or near the 3'-end of said oligonucleotide that it hybridizes to said oligonucleotide at a preselected temperature, a second oligonucleotide primer that has a sequence substantially identical to a portion of said oligonucleotide at or near its 5'-end, and 2'-deoxynucleoside triphosphates selected from the group consisting of 2'-deoxyadenosine triphosphate, 2'-deoxyguanosine triphosphate, 2'-deoxycytidine triphosphate, thymidine triphosphate,

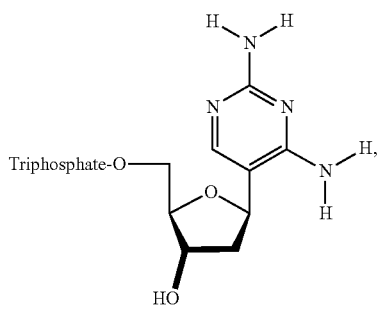

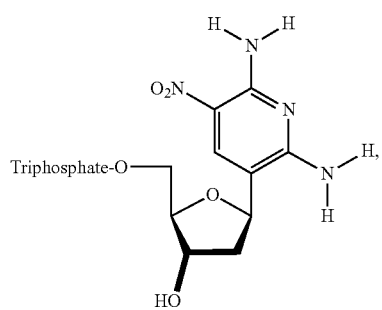

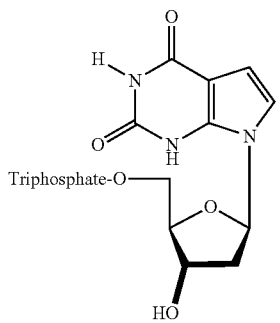

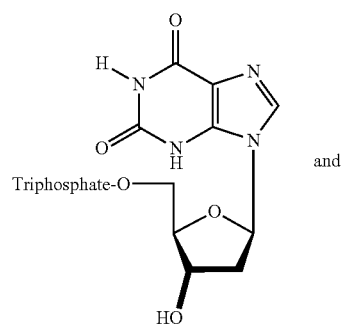

and (b) incubating said mixture at said preselected temperature where said polymerase extends the first oligonucleotide primer to give an extension product that is substantially complementary to said oligonucleotide, wherein said extension product forms a duplex with said oligonucleotide, such that said extension product, when it is separated from said oligonucleotide, can hybridize with the second primer, (c) increasing the temperature of said mixture to a temperature sufficient to separate said oligonucleotide from said extension product, (d) lowering the temperature of said mixture to a preselected temperature at which the first oligonucleotide primer hybridizes to said oligonucleotide and said second oligonucleotide primer can hybridize to said extension product, and (e) repeating steps (b) through (d).

\* \* \* \* \*